(12) United States Patent
Ng et al.

(10) Patent No.: US 6,515,162 B2
(45) Date of Patent: Feb. 4, 2003

(54) METHOD OF PREPARING RETROVIRAL PROTEASE INHIBITOR INTERMEDIATES

(75) Inventors: John S Ng, Chicago, IL (US); Claire S. Przybyla, Des Plaines, IL (US); Shu-Hong Zhang, Groton, CT (US)

(73) Assignee: G.D. Searle & Co., Chicago, IL (US)

( * ) Notice: Subject to any disclaimer, the term of this patent is extended or adjusted under 35 U.S.C. 154(b) by 0 days.

(21) Appl. No.: 09/741,087

(22) Filed: Dec. 21, 2000

(65) Prior Publication Data

US 2001/0047111 A1 Nov. 29, 2001

Related U.S. Application Data

(60) Continuation of application No. 09/024,662, filed on Feb. 17, 1998, now Pat. No. 6,201,150, which is a division of application No. 08/376,340, filed on Jan. 20, 1995, now Pat. No. 5,831,117.

(51) Int. Cl.$^7$ ............................................. C07C 255/43
(52) U.S. Cl. ................... 558/390; 546/146; 558/408
(58) Field of Search ........................ 546/146; 558/390, 558/408

(56) References Cited

U.S. PATENT DOCUMENTS

| | | |
|---|---|---|
| 4,267,332 A | 5/1981 | Nohara et al. |
| 4,268,688 A | 5/1981 | Tinker et al. |
| 4,477,414 A | 10/1984 | Boger et al. |
| 4,514,391 A | 4/1985 | Gordon et al. |
| 4,548,926 A | 10/1985 | Matsueda et al. |
| 4,599,198 A | 7/1986 | Hoover |
| 4,616,088 A | 10/1986 | Ryono et al. |
| 4,668,769 A | 5/1987 | Hoover |
| 4,668,770 A | 5/1987 | Boger et al. |
| 4,757,050 A | 7/1988 | Natarajan et al. |
| H725 H | 1/1990 | Gordon |
| 4,963,530 A | 10/1990 | Hemmi et al. |
| 4,977,277 A | 12/1990 | Rosenberg et al. |
| 4,990,669 A | 2/1991 | Reetz et al. |
| 5,157,041 A | 10/1992 | Handa et al. |
| 5,641,886 A * | 6/1997 | Hilpert ...................... 546/146 |

FOREIGN PATENT DOCUMENTS

| | | |
|---|---|---|
| AU | 79823/87 | 10/1987 |
| EP | 0 104 041 | 3/1984 |
| EP | 0 172 347 | 2/1986 |
| EP | 0 223 437 | 5/1987 |
| EP | 0 264 795 | 4/1988 |
| EP | 0 337 714 | 10/1989 |
| EP | 0 342 541 | 11/1989 |
| EP | 0 356 223 | 2/1990 |
| EP | 389898 | 10/1990 |
| EP | 0 389 898 | 10/1990 |
| EP | 0 402 646 | 12/1990 |
| EP | 468641 | 1/1992 |
| GB | 2184730 | 7/1987 |
| GB | 2209752 | 5/1989 |
| WO | 84/03044 | 8/1964 |
| WO | 94/05639 | 10/1990 |
| WO | 92/08701 | 5/1992 |
| WO | 93/23388 | 11/1993 |
| WO | 0 393 445 | 3/1994 |
| WO | 94/04492 | 3/1994 |
| WO | 94/12201 | 6/1994 |
| WO | 95/14653 | 6/1995 |

OTHER PUBLICATIONS

International Search Report of PCT/US96/00918 dated Jan. 18, 1996.
Getman, et al., *J. Med. Chem.*, 36, 288 (1993).
Reetz, et al., *Tet. Lett.*, 30, 5425 (1989).
Reetz, et al., *Angew. Chem. Int. Ed.*, 26, 1141–1143 (1987).
Rosenberg et al., *J. Med. Chem.*, 30, 1224–1228, (1987).

* cited by examiner

*Primary Examiner*—Robert Gerstl
(74) *Attorney, Agent, or Firm*—Banner & Witcoff, Ltd.

(57) ABSTRACT

Chiral hydroxyethylamine, hydroxyethylurea or hydroxyethylsulfonamide isostere containing retroviral protease and renin inhibitors can be prepared by multi-step syntheses that utilize key chiral amine intermediates. This invention is a cost effective method of obtaining such key chiral amine intermediates enantiomerically, diastereomerically and chemically pure. The method is suitable for large scale (multikilogram) productions. This invention also encompasses organic acid and inorganic acid salts of the amine intermediates.

10 Claims, No Drawings

METHOD OF PREPARING RETROVIRAL PROTEASE INHIBITOR INTERMEDIATES

This application is a continuation of application Ser. No. 09/024,662, filed Feb. 17, 1998, now U.S. Pat. No. 6,201,150, which is a division of application Ser. No. 08/376,340, filed Jan. 20, 1995, now U.S. Pat. No. 5,831,117.

BACKGROUND OF THE INVENTION

Synthesis of many retroviral protease and renin inhibitors containing a hydroxyethylamine, hydroxyethylurea or hydroxyethylsulfonamide isostere include the preparation of a key chiral amine intermediate. The synthesis of the key chiral amine requires a multi-step synthesis starting from a chiral amino acid such as L-phenylalanine. The key chiral amine intermediate can be prepared by diastereoselective reduction of an intermediate amino chloromethylketone or amine opening of a chiral epoxide intermediate. The present invention relates to a cost effective method of obtaining enantiomerically, diastereomerically and chemically pure chiral amine intermediate. This method is applicable for large scale (multikilogram) productions.

Roberts et al. (*Science*, 248, 358 (1990)), Krohn et al. (*J. Med. Chem.* 344, 3340 (1991)) and Getman et al. (*J. Med. Chem.*, 346, 288 (1993)) disclosed the synthesis of protease inhibitors containing the hydroxyethylamine or hydroxyethylurea isostere which include the opening of an epoxide generated in a multi-step synthesis starting from an amino acid. These methods also contain steps which include diazomethane and the reduction of an amino chloromethyl ketone intermediate to an amino alcohol prior to formation of the epoxide. The overall yield of these syntheses are low and the use of explosive diazomethane additionally prevents such methods from being commercially acceptable.

Tinker et al. (U.S. Pat. No. 4,268,688) disclosed a catalytic process for the asymmetric hydroformylation to prepare optically active aldehydes from unsaturated olefins. Similarly, Reetz et al. (U.S. Pat. No. 4,990,669) disclosed the formation of optically active alpha amino aldehydes through the reduction of alpha amino carboxylic acids or their esters with lithium aluminum hydride followed by oxidation of the resulting protected beta amino alcohol by dimethyl sulfoxide/oxalyl chloride or chromium trioxide/pyridine. Alternatively, protected alpha amino carboxylic acids or esters thereof can be reduced with diisobutylaluminum hydride to form the protected amino aldehydes.

Reetz et al. (Tet. Lett., 30, 5425 (1989)) disclosed the use of sulfonium and arsonium ylides and their reactions of protected α-amino aldehydes to form aminoalkyl epoxides. This method suffers from the use of highly toxic arsonium compounds or the use of combination of sodium hydride and dimethyl sulfoxide which is extremely hazardous in large scale. Sodium hydride and DMSO are incompatible (Sax, N. I., "Dangerous Properties of Industrial Materials", 6th Ed., Van Nostrand Reinhold Co., 1984, p. 433). Violent explosions have been reported on the reaction of sodium hydride and excess DMSO ("Handbook of Reactive Chemical Hazards", 3rd Ed., Butterworths, 1985, p. 295).

Matteson et al. (*Synlett.*, 1991, 631) reported the addition of chloromethyllithium or bromomethyllithium to racemic aldehydes. J. Ng et al. (WO 93/23388 and PCT/US94/12201, both incorporated herein by reference in their entirety) disclose methods of preparing chiral epoxide, chiral cyanohydrin, chiral amine and other chiral intermediates useful in the preparation of retroviral protease inhibitors.

Various enzyme inhibitors, such as renin inhibitors and HIV protease inhibitors, have been prepared using the above described methods or variations thereof. EP 468641, EP 223437, EP 389898 and U.S. Pat. No. 4,599,198 for example describe the preparation of hydroxyethylamine isostere containing renin inhibitors. U.S. Pat. No. 5,157,041, WO 94/04492 and WO 92/08701 (each of which is incorporated herein by reference in its entirety) for example describe the preparation of hydroxyethylamine, hydroxyethylurea or hydroxyethylsulfonamide isostere containing retroviral protease inhibitors.

SUMMARY OF THE INVENTION

Human immunodeficiency virus (HIV), the causative agent of acquired immunodeficiency syndrome (AIDS), encodes three enzymes, including the well-characterized proteinase belonging to the aspartic proteinase family, the HIV protease. Inhibition of this enzyme is regarded as a promising approach for treating AIDS. One potential strategy for inhibitor design involves the introduction of hydroxyethylene transition-state analogs into inhibitors. Inhibitors adapting a hydroxyethylamine, hydroxyethylurea or hydroxyethylsulfonamide isostere are found to be highly potent inhibitors of HIV proteases. Despite the potential clinical importance of these compounds, the synthesis of these compounds are difficult and costly due to the number of chiral centers. Efficient processes for preparing large scale (multikilogram quantities) of such inhibitors is needed for development, clinical studies and cost effective pharmaceutical preparations.

This invention improves the synthesis of intermediates which are readily amenable to the large scale preparation of chiral hydroxyethylamine, hydroxyethylurea or hydroxyethylsulfonamide retroviral protease, renin or other aspartyl protease inhibitors. Specifically, the method includes precipitating, crystallizing or recrystallizing a salt of the desired chiral amine intermediate.

DETAILED DESCRIPTION OF THE INVENTION

This invention relates to a method of preparation of retroviral protease inhibitor that allows the preparation of commercial quantities of intermediates of the formulae

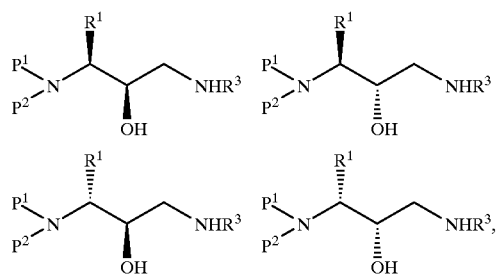

wherein $R^1$, $R^3$, $P^1$ and $P^2$ are as defined below. Typical preparations of one diastereomer from enantiomerically pure starting materials, such as L-phenylalanine or D-phenylalanine, using methods as described herein and elsewhere result in enantiomeric mixtures of the alcohol containing carbon (—CHOH—) ranging from about 50:50 to about 90:10. Isolation of the desired enantiomer usually involves chromatographic separation. Alternatively, the enantiomeric mixture is used without separation and enantiomerically pure material is obtained at a later step in the synthesis of the inhibitors. These approaches increase the time and cost involved in the manufacture of a pharmaceutical preparation. Chromatographic separations increase the cost of manufacture. Using impure materials increases the amount of other reactants used in later steps of the inhibitor synthesis, and increases the amount of side products and waste produced in the later steps. Furthermore, these compounds often show indications of poor stability and may not be suitable for storage or shipment in large quantity (multikilograms) for long periods of time. Storage and shipment stability of such compounds is particularly important when the manufacture of the pharmaceutical preparation is carried out at different locations and/or in different environments. Alternatively, the amine can be protected with an amine protecting group, such as tert-butoxycarbonyl, benzyloxycarbonyl and the like, as described below and purified, such as by chromatography, crystallization and the like, followed by deprotection of the amine. This alternative adds more steps to the overall synthesis of the inhibitors and increases the manufacturing costs.

The present invention relates to a simple, economical process of isolating substantially enantiomerically and/or diastereomerically pure forms of Formula I. The process involves forming and isolating a salt of Formula I from crude reaction mixtures. The salt can be formed in the reaction mixture from which it precipitates. The precipitate can then be crystallized or recrystallized from the appropriate solvent system, such as ethanol, methanol, heptane, hexane, dimethylether, methyl-tert-butylether, ethyl acetate and the like or mixtures thereof. Alternatively, the reaction mixture solvent can be removed, such as in vacuo, and dissolved in a more appropriate solvent or mixture of solvents, such as methanol, ethanol, toluene, xylene, methylene chloride, carbon tetrachloride, hexane, heptane, petroleum ethers, dimethylether, ethyl acetate, methyl-tert-butylether, tetrahydrofuran, and the like or mixtures thereof. This may also permit removal, such as by filtration or extraction, of undesired materials from the reaction mixture, such as salts, side products, and the like. After the crude reaction mixture is dissolved, then the salt of Formula I can be precipitated or crystallized and recrystallized if desired or necessary. Formation, precipitation, crystallization and/or recrystallization of such salts can also be accomplished using water and water miscible or soluble organic solvent(s) mixtures, such as water/methanol, water/ethanol, and the like.

A salt of Formula I is prepared by the addition of an organic or inorganic acid, preferably in at least an equimolar quantities and more preferably in greater than equimolar quantities, directly to the reaction mixture or to the crude reaction mixture in solution as described above. Such salts may be monovalent, divalent or trivalent acid salts, may be monoprotic, diprotic, or triprotic, may be mixed or complex salts, or combinations thereof. Preferred organic acids which may be employed to form salts of Formula I include but are not limited to the following: acetic acid, aconitatoc acid, adipic acid, alginic acid, citric acid, aspartic acid, benzoic acid, benzenesulfonic acid, butyric acid, camphoric acid, camphorsulfonic acid, digluconic acid, isocitric acid, cyclopentylpropionic acid, undecanoic acid, malaic acid, dodecylsulfonic acid, ethanesulfonic acid, malic acid, glucoheptanoic acid, heptanoic acid, hexanoic acid, fumaric acid, 2-hydroxyethanesulfonic acid, lactic acid, maleic acid, mandelic acid, methanesulfonic acid, nicotinic acid, oxalacetic acid, 2-naphthalenesulfonic acid, oxalic acid, palmitic acid, pectinic acid, 3-phenylpropionic acid, picric acid, pivalic acid, propionic acid, succinic acid, glycerophosphoric acid, tannic acid, trifluoroacetic acid, toluenesulfonic acid, tartaric acid, diacetyltartaric acid, dibenzoyltartaric acid, ditoluyltartaric acid and the like. More preferred organic acids include acetic acid, camphorsulfonic acid, toluenesulfonic acid, methanesulfonic acid, malic acid, tartaric acid, mandelic acid, trifluoroacetic acid and oxalic acid. Most preferred organic acids include acetic acid, oxalic acid and tartaric acid. Racemic mixtures or optically pure isomers of an organic acid may be used, such as D, L, DL, meso, erythro, threo, and the like isomers. Preferred inorganic acids which may be employed to form salts of Formula I include but are not limited to the following: hydrochloric acid, hydrobromic acid, phosphoric acid, sulfurous acid, sulfuric acid and the like. A more preferred inorganic acid is hydrochloric acid.

The salts of Formula I and in particular crystalline salts of Formula I of the present invention are typically more stable under normal storage and shipping conditions than Formula I.

Formula I of the present invention means the formula

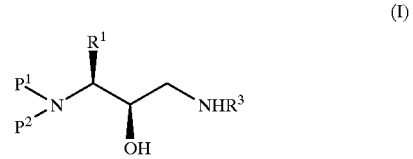

(I)

wherein $R^1$ represents alkyl, aryl, cycloalkyl, cycloalkylalkyl or aralkyl radicals, which are optionally substituted with alkyl, halogen, $NO_2$, $OR^9$ or $SR^9$, where $R^9$ represents hydrogen, alkyl, aryl or aralkyl. Preferably, $R^1$ is alkyl, cycloalkylalkyl or aralkyl radicals, which are optionally substituted with alkyl, halogen, $NO_2$, $OR^9$ or $SR^9$, where $R^9$ represents hydrogen, alkyl, aryl or aralkyl. Most preferably, $R^1$ is 2-(methylthio)ethyl, phenylthiomethyl, benzyl, (4-fluorophenyl)methyl, 2-naphthylmethyl or cyclohexylmethyl radicals.

$R^3$ represents hydrogen, alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl or N-mono- or N,N-disubstituted aminoalkyl radicals, wherein said substituents are alkyl, aryl, aralkyl, cycloalkyl, cycloalkylalkyl, heteroaryl, heteroaralkyl, heterocycloalkyl, or heterocycloalkylalkyl radicals, or in the case of a disubstituted aminoalkyl radical, said substituents along with the nitrogen atom to which they are attached, form a heterocycloalkyl or a heteroaryl radical. Preferably, $R^3$ represents hydrogen, alkyl, cycloalkyl, cycloalkylalkyl or aralkyl radicals. More preferably, $R^3$ represents hydrogen, propyl, butyl, isobutyl, isoamyl, cyclopentyl, cyclohexyl, cycloheptyl, cyclohexylmethyl, cyclopentylmethyl, phenylethyl or benzyl radicals. Most preferably, $R^3$ represents radicals as defined above which contain no alpha-branching, e.g., as in an isopropyl radical or a t-butyl radical. The preferred radicals are those which contain a —$CH_2$— moiety between the nitrogen and the remaining portion of the radical. Such preferred groups include, but are not limited to, benzyl, isobutyl, n-butyl, isoamyl, cyclohexylmethyl, cyclopentylmethyl and the like.

$P^1$ and $P^2$ are each independently hydrogen or amine protecting groups, including but not limited to, aralkyl, substituted aralkyl, cycloalkenylalkyl and substituted cycloalkenylalkyl, allyl, substituted allyl, acyl, alkoxycarbonyl, aralkoxycarbonyl and silyl. Examples of aralkyl include, but are not limited to benzyl, 1-phenylethyl, ortho-methylbenzyl, trityl and benzhydryl, which can be optionally substituted with halogen, alkyl of $C_1$–$C_8$, alkoxy, hydroxy, nitro, alkylene, acylamino and acyl. Examples of aryl groups include phenyl, naphthalenyl, indanyl, anthracenyl, durenyl, 9-(9-phenylfluorenyl) and phenanthrenyl, which can be optionally substituted with halogen, alkyl of $C_1$–$C_8$, alkoxy, hydroxy, nitro, alkylene, acylamino and acyl. Suitable acyl groups include carbobenzoxy, t-butoxycarbonyl, iso-butoxycarbonyl, benzoyl, substituted benzoyl such as 2-methylbenzoyl, 2,6-dimethylbenzoyl 2,4,6-trimethylbenzoyl and 2,4,6-triisopropylbenzoyl, 1-naphthoyl, 2-naphthoyl butyryl, acetyl, tri-fluoroacetyl, tri-chloroacetyl, phthaloyl and the like.

Additionally, $P^1$ and $P^2$ protecting groups can form a heterocyclic ring system with the nitrogen to which they are attached, for example, 1,2-bis(methylene)benzene (i.e., 2-isoindolinyl), phthalimidyl, succinimidyl, maleimidyl and the like and where these heterocyclic groups can further include adjoining aryl and cycloalkyl rings. In addition, the heterocyclic groups can be mono-, di- or tri-substituted, e.g., nitrophthalimidyl.

Suitable carbamate protecting groups include, but are not limited to, methyl and ethyl carbamate; 9-fluorenylmethyl carbamate; 9-(2-Sulfo)fluorenylmethyl carbamate; 9-(2,7-dibromo)fluorenylmethyl carbamate; 2,7-di-t-butyl-[9-(10,10-dioxo-10,10,10-tetrahydrothioxanthyl)methyl carbamate; 4-methoxyphenacyl carbamate; 2,2,2-trichloroethyl carbamate; 2-trimethylsilylethyl carbamate; 2-phenylethyl carbamate; 1-(1-adamantyl)-1-methylethyl carbamate; 1,f-dimethyl-2-haloethyl carbamate; 1,1-dimethyl-2,2-dibromoethyl carbamate; 1,1-dimethyl-2,2,2-trichloroethyl carbamate; 1-methyl-1-(4-biphenylyl)-ethyl carbamate; 1-(3,5-di-t-butylphenyl)-1-methylethyl carbamate; 2-(2'-and 4'-pyridyl)ethyl carbamate; 2-(N,N-dicyclohexylcarboxamido)ethyl carbamate; t-butyl carbamate; 1-adamantyl carbamate; vinyl carbamate; allyl carbamate; 1-isopropylallyl carbamate; cinnamyl carbamate; 4-nitrocinnamyl carbamate; 8-quinolyl carbamate; N-hydroxypiperidinyl carbamate; alkyldithio carbamate; benzyl carbamate; p-methoxybenzyl carbamate; p-nitrobenzyl carbamate; p-bromobenzyl carbamate; p-chlorobenzyl carbamate; 2,4-dichlorobenzyl carbamate; 4-methylsulfinylbenzyl carbamate; 9-anthrylmethyl carbamate; diphenylmethyl carbamate; 2-methylthioethyl carbamate; 2-methylsulfonylethyl carbamate; 2-(p-toluenesulfonyl) ethyl carbamate; [2-(1,3-dithianyl)methyl carbamate; 4-methylthiophenyl-2,4-dimethylthiophenyl, 2-phosphonioethyl carbamate; 2-triphenylphosphonioisopropyl carbamate; 1,1-dimethyl-2-cyanoethyl carbamate; m-chloro-p-acyloxybenzyl carbamate; p-(dihydroxyboryl)benzyl carbamate; 5-benzoisoxazolylmethyl carbamate; 2-(trifluoromethyl)-6-chromonylmethyl carbamate; m-nitrophenyl carbamate; 3,5-dimethoxybenzyl carbamate; o-nitrobenzyl carbamate; 3,4-dimethoxy-6-nitrobenzyl carbamate; phenyl(o-nitrophenyl) methyl carbamate; phenothiazinyl-(10)-carbonyl derivative; N'-p-toluenesulfonylaminocarbonyl derivative; N'-phenylaminothiocarbonyl derivative t-amyl carbamate; S-benzyl thiocarbamate; p-cyanobenzyl carbamate; cyclobutyl carbamate; cyclohexyl carbamate; cyclopentyl carbamate; cyclopropylmethyl carbamate; p-decyloxybenzyl carbamate; diisopropylmethyl carbamate; 2,2-dimethoxycarbonylvinyl carbamate; o-(N,N-dimethylcarboxamido)benzyl carbamate; 1,1-dimethyl-3-(N,N-dimethylcarboxamido)propyl carbamate; 1,1-dimethylpropynyl carbamate; di(2-pyridyl)methyl carbamate; 2-furanylmethyl carbamate; 2-iodoethyl carbamate; isobornyl carbamate; isobutyl carbamate; isonicotinyl carbamate; p-(p'-methoxyphenylazo)benzyl carbamate; 1-methylcyclobutyl carbamate; 1-methylcyclohexyl carbamate; 1-methyl-1-cyclopropylmethyl carbamate; 1-methyl-1-(3,5-dimethoxyphenyl)ethyl carbamate; 1-methyl-1-(p-phenylazophenyl)ethyl carbamate; and 1-methyl-1-phenylethyl carbamate. T. Greene and P. Wuts ("Protective Groups In Organic Synthesis," 2nd Ed., John Wiley & Sons, Inc. (1991)) describe the preparation and cleavage of such carbamate protecting groups.

The term silyl refers to a silicon atom substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis (dimethylsilyl)ethane and diphenylmethylsilyl. Silylation of the amine functions to provide mono- or bis-disilylamine can provide derivatives of the aminoalcohol, amino acid, amino acid esters and amino acid amide. In the case of amino acids, amino acid esters and amino acid amides, reduction of the carbonyl function provides the required mono- or bis-silyl aminoalcohol. Silylation of the aminoalcohol can lead to the N,N,O-tri-silyl derivative. Removal of the silyl function from the silyl ether function is readily accomplished by treatment with, for example, a metal hydroxide or ammonium fluoride reagent, either as a discrete reaction step or in situ during the preparation of the amino aldehyde reagent. Suitable silylating agents are, for example, trimethylsilyl chloride, tert-buty-dimethylsilyl chloride, phenyldimethylsilyl chloride, diphenylmethylsilyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Preferably $P^1$ is aralkyl, substituted aralkyl, alkylcarbonyl, aralkylcarbonyl, arylcarbonyl, alkoxycarbonyl or aralkoxycarbonyl, and $P^2$ is aralkyl or substituted aralkyl. Alternatively, when $P^1$ is alkoxycarbonyl or aralkoxycarbonyl, $P^2$ can be hydrogen. More preferably, $P^1$ is t-butoxycarbonyl, phenylmethoxycarbonyl, (4-methoxyphenyl)methoxycarbonyl or benzyl, and $P^2$ is hydrogen or benzyl.

Because the same synthetic and purification procedures are applicable to the preparation of each of the four possible diastereomers of Formula I, provided the proper chiral amino acid starting material is utilized, Formula I though shown in one configuration is intended to encompass all four diastereomers individually. Thus, the preparation procedures described herein and the definitions of $R^1$, $R^3$, $P^1$ and $P^2$ also apply to the other three configurational isomers

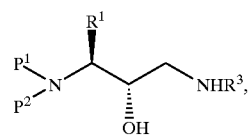

IB

-continued

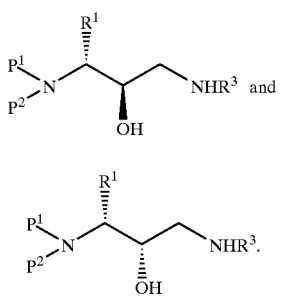

(IC)

(ID)

Protected amino epoxides of the formula

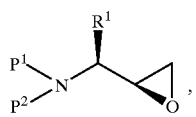

(IV)

protected amino alpha-hydroxycyanides and acids of the formula

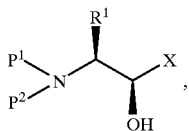

wherein X is —CN, —CH$_2$NO$_2$ or —COOH, protected alpha-aminoaldehyde intermediates of the formula

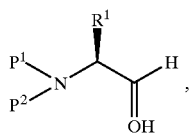

(III)

and protected chiral alpha-amino alcohols of the formula

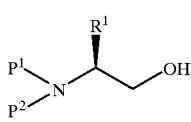

(II)

wherein P$^1$, P$^2$ and R$^1$ are as defined above, are also described herein.

As utilized herein, the term "amino epoxide" alone or in combination, means an amino-substituted alkyl epoxide wherein the amino group can be a primary, or secondary amino group containing substituents selected from hydrogen, alkyl, aryl, aralkyl, alkenyl, alkoxycarbonyl, aralkoxycarbonyl, cycloalkenyl, silyl, cycloalkylalkenyl radicals and the like and the epoxide can be alpha to the amine. The term "amino aldehyde" alone or in combination, means an amino-substituted alkyl aldehyde wherein the amino group can be a primary, or secondary amino group containing substituents selected from hydrogen, alkyl, aryl, aralkyl, alkenyl, aralkoxycarbonyl, alkoxycarbonyl, cycloalkenyl, silyl, cycloalkylalkenyl radicals and the like and the aldehyde can be alpha to the amine. The term "alkyl", alone or in combination, means a straight-chain or branched-chain alkyl radical containing from 1 to 10, preferably from 1 to 8, more preferably from 1 to 5 carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "alkenyl", alone or in combination, means a straight-chain or branched-chain hydrocarbon radial having one or more double bonds and containing from 2 to 10 carbon atoms, preferably from 2 to 8, more preferably from 2 to 5 carbon atoms. Examples of suitable alkenyl radicals include ethenyl, propenyl, allyl, 1,4-butadienyl and the like. The term "alkynyl", alone or in combination, means a straight-chain hydrocarbon radical having one or more triple bonds and containing from 2 to about 10, preferably from 2 to 8, more preferably from 2 to 5 carbon atoms. Examples of alkynyl radicals include ethynyl, propynyl, (propargyl), butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkenyl", alone or in combination, means an alkyl radical which contains from 5 to 8, preferably 5 to 6 carbon atoms, is cyclic and contains at least one double bond in the ring which is non-aromatic in character. Examples of such cycloalkenyl radicals include cyclopropenyl, cyclobutenyl, cyclopentenyl, cyclohexenyl, dihydrophenyl and the like. The term "cycloalkenylalkyl", means cycloalkenyl radical as defined above which is attached to an alkyl radical as defined above. The term "cycloalkyl", alone or in combination, means a cyclic alkyl radical which contains from about 3 to about 8, preferably 3 to 6, more preferably 5 to 6 carbon atoms. The term "cycloalkylalkyl" means an alkyl radical as defined above which is substituted by a cycloalkyl radical as defined above. Examples of such cycloalkyl radicals include cyclopropyl, cyclobutyl, cyclopentyl, cyclohexyl and the like. The term "aryl", alone or in combination, means a phenyl or naphthyl radical either of which is optionally substituted by one or more alkyl, alkoxy, halogen, hydroxy, amino, nitro and the like, as well as p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. The term "aralkyl", alone or in combination, means an alkyl radical as defined above substituted by an aryl radical as defined above, such as benzyl, 1-phenylethyl and the like. Examples of substituted aralkyl include 3,5-dimethoxybenzyl, 3,4-dimethoxybenzyl, 2,4-dimethoxybenzyl, 3,4,5-trimethoxybenzyl, 4-nitrobenzyl, 2,6-dichlorobenzyl, 4-(chloromethyl)benzyl, 2-(bromomethyl)benzyl, 3-(chloromethyl)benzyl, 4-chlorobenzyl, 3-chlorobenzyl, 2-(chloromethyl)benzyl, 6-chloropiperonyl, 2-chlorobenzyl, 4-chloro-2-nitrobenzyl, 2-chloro-6-fluorobenzyl, 2-(chloromethyl)-4,5-dimethylbenzyl, 6-(chloromethyl)duren-3-ylmethyl, 10-(chloromethyl)anthracen-9-ylmethyl, 4-(chloromethyl)-2,5-dimethylbenzyl, 4-(chloromethyl)-2, 5-dimethoxybenzyl, 4-(chloromethyl)anisol-2-ylmethyl, 5-(chloromethyl)-2,4-dimethylbenzyl, 4-(chloromethyl)mesitylen-2-ylmethyl, 4-acetyl-2,6-dichlorobenzyl, 2-chloro-4-methylbenzyl, 3,4-dichlorobenzyl, 6-chlorobenzo-1,3-dioxan-8-ylmethyl, 4-(2,6-dichlorobenzylsulphonyl)benzyl, 4-chloro-3-nitrobenzyl, 3-chloro-4-methoxybenzyl, 2-hydroxy-3-(chloromethyl)-5-methylbenzyl and the like. The term aralkoxycarbonyl means an aralkoxyl group attached to a carbonyl. Carbobenzoxy is an example of aralkoxycarbonyl. The term "heterocyclic" means a saturated or partially unsaturated monocyclic, bicyclic or tricyclic heterocycle having 5 to 6 ring members in each ring and which contains one or more heteroatoms as ring atoms, selected from nitrogen, oxygen, silicon and sulphur, which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e. =N—) by oxido. "Heteroaryl" means an aromatic monocyclic, bicyclic, or tricyclic heterocycle which contains the heteroatoms and is optionally substituted as defined above with respect to the definition of aryl. Examples of such heterocyclic groups are pyrrolidinyl, piperidinyl, piperazinyl, morpholinyl, thiamorpholinyl, pyrrolyl, phthalimide, succinimide, maleimide, and the like. Also included are heterocycles containing two silicon atoms simultaneously attached to the nitrogen and joined by carbon atoms. The term "alkylamino" alone or in combination, means an amino-substituted alkyl group wherein the amino group can be a primary, or secondary amino group containing substituents selected from hydrogen, alkyl, aryl, aralkyl, cycloalkyl, cycloalkylalkyl radicals and the like. The term "halogen" means fluorine, chlorine, bromine or iodine. The term dihaloalkyl means two halogen atoms, the same or different, substituted on the same carbon atom. The term "oxidizing agent" includes a single agent or a mixture of oxidizing reagents. Examples of mixtures of oxidizing reagents include sulfur trioxide-pyridine/dimethylsulfoxide, oxalyl chloride/dimethyl sulfoxide, acetyl chloride/dimethyl sulfoxide, acetyl anhydride/dimethyl sulfoxide, trifluoroacetyl chloride/dimethyl sulfoxide, toluenesulfonyl bromide/dimethyl sulfoxide, phosphorous pentachloride/dimethyl sulfoxide and isobutylchloroformate/dimethyl sulfoxide.

A general Scheme for the preparation of amino epoxides, useful as intermediates in the synthesis of HIV protease inhibitors is shown in Scheme 1 below.

Scheme I

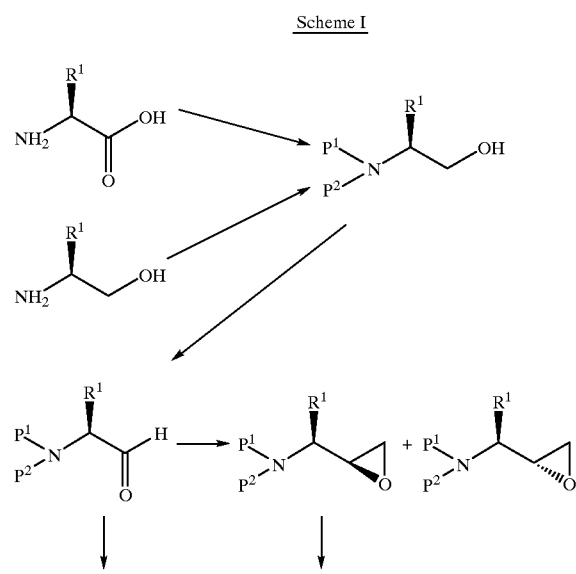

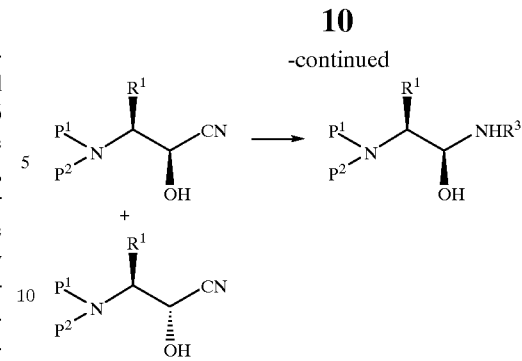

An economical and safe large scale method of preparation of protease inhibitors of the present invention can alternatively utilize amino acids or amino alcohols to form N,N-protected alpha aminoalcohol of the formula

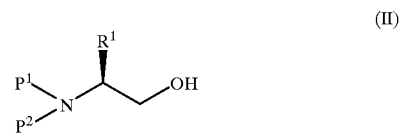

(II)

wherein $P^1$, $P^2$ and $R^1$ are described above.

Whether the compounds of Formula II are formed from amino acids or aminoalcohols, such compounds have the amine protected with groups $P^1$ and $P^2$ as previously identified. The nitrogen atom can be alkylated such as by the addition of suitable alkylating agents in an appropriate solvent in the presence of base.

Alternate bases used in alkylation include sodium hydroxide, sodium bicarbonate, potassium hydroxide, lithium hydroxide, potassium carbonate, sodium carbonate, cesium hydroxide, magnesium hydroxide, calcium hydroxide or calcium oxide, or tertiary amine bases such as triethyl amine, diisopropylethylamine, pyridine, N-methylpiperidine, dimethylaminopyridine and azabicyclononane. Reactions can be homogenous or heterogenous. Suitable solvents are water and protic solvents or solvents miscible with water, such as methanol, ethanol, isopropyl alcohol, tetrahydrofuran and the like, with or without added water. Dipolar aprotic solvents may also be used with or without added protic solvents including water. Examples of dipolar aprotic solvents include acetonitrile, dimethylformamide, dimethyl acetamide, acetamide, tetramethyl urea and its cyclic analog, dimethylsulfoxide, N-methylpyrrolidone, sulfolane, nitromethane and the like. Reaction temperature can range between about −20° to 100° C. with the preferred temperature of about 25–85° C. The reaction may be carried out under an inert atmosphere such as nitrogen or argon, or normal or dry air, under atmospheric pressure or in a sealed reaction vessel under positive pressure. The most preferred alkylating agents are benzyl bromide or benzyl chloride or monosubstituted aralkyl halides or polysubstituted aralkyl halides. Sulfate or sulfonate esters are also suitable reagents to provide the corresponding benzyl analogs and they can be preformed from the corresponding benzyl alcohol or formed in situ by methods well known to those skilled in the art. Trityl, benzhydryl, substituted trityl and substituted benzhydryl groups, independently, are also effective amine protecting groups [$P^1$, $P^2$] as are allyl and substituted allyl groups. Their halide derivatives can also be prepared from the corresponding alcohols by methods well known to those skilled in the art such as treatment with thionyl chloride or bromide or with phosphorus tri- or pentachloride, bromide or iodide or the corresponding phosphoryl trihalide. Examples of groups that can be substituted on the aryl ring include alkyl, alkoxy, hydroxy, nitro, halo and alkylene, amino, mono- and dialkyl amino and acyl amino, acyl and water solubilizing groups such as phosphonium salts and ammonium salts. The aryl ring can be derived from, for example, benzene, napthelene, indane, anthracene, 9-phenylfluorenyl, durene, phenanthrene and the like. In addition, 1,2-bis (substituted alkylene) aryl halides or sulfonate esters can be used to form a nitrogen containing aryl or non-aromatic heterocyclic derivative [with $P^1$ and $P^2$] or bis-heterocycles. Cycloalkylenealkyl or substituted cyloalkylene radicals containing 6–10 carbon atoms and alkylene radicals constitute additional acceptable class of substituents on nitrogen prepared as outlined above including, for example, cyclohexylenemethylene.

Compounds of Formula II can also be prepared by reductive alkylation by, for example, compounds and intermediates formed from the addition of an aldehyde with the amine and a reducing agent, reduction of a Schiff Base, carbinolamine or enamine or reduction of an acylated amine derivative. Reducing agents include metals [platinum, palladium, palladium hydroxide, palladium on carbon, platinum oxide, rhodium and the like] with hydrogen gas or hydrogen transfer molecules such as cyclohexene or cyclohexadiene or hydride agents such as lithium aluminum hydride, sodium borohydride, lithium borohydride, sodium cyanoborohydride, diisobutylaluminum hydride or lithium tri-tert-butoxyaluminum hydride.

Additives such as sodium or potassium bromide, sodium or potassium iodide can catalyze or accelerate the rate of amine alkylation, especially when benzyl chloride was used as the nitrogen alkylating agent.

Phase transfer catalysis wherein the amine to be protected and the nitrogen alkylating agent are reacted with base in a solvent mixture in the presence of a phase transfer reagent, catalyst or promoter. The mixture can consist of, for example, toluene, benzene, ethylene dichloride, cyclohexane, methylene chloride or the like with water or a aqueous solution of an organic water miscible solvent such as THF. Examples of phase transfer catalysts or reagents include tetrabutylammonium chloride or iodide or bromide, tetrabutylammonium hydroxide, tri-butyloctylammonium chloride, dodecyltrihexylammonium hydroxide, methyltrihexylammonium chloride and the like.

A preferred method of forming substituted amines involves the aqueous addition of about 3 moles of organic halide to the amino acid or about 2 moles to the aminoalcohol. In a more preferred method of forming a protected amino alcohol, about 2 moles of benzylhalide in a basic aqueous solution is utilized. In an even more preferred method, the alkylation occurs at 50° C. to 80° C. with potassium carbonate in water, ethanol/water or denatured ethanol/water. In a more preferred method of forming a protected amino acid ester, about 3 moles of benzylhalide is added to a solution containing the amino acid.

The protected amino acid ester is additionally reduced to the protected amino alcohol in an organic solvent. Preferred reducing agents include lithium aluminum hydride, lithium borohydride, sodium borohydride, borane, lithium tri-tert-butoxyaluminum hydride, borane·THF complex. Most preferably, the reducing agent is diisobutylaluminum hydride (DiBAL-H) in toluene. These reduction conditions provide an alternative to a lithium aluminum hydride reduction.

Purification by chromatography is possible. In the preferred purification method the alpha amino alcohol can be purified by an acid quench of the reaction, such as with hydrochloric acid, and the resulting salt can be filtered off as a solid and the amino alcohol can be liberated such as by acid/base extraction.

The protected alpha amino alcohol is oxidized to form a chiral amino aldehyde of the formula

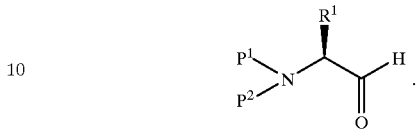

Acceptable oxidizing reagents include, for example, sulfur trioxide-pyridine complex and DMSO, oxalyl chloride and DMSO, acetyl chloride or anhydride and DMSO, trifluoroacetyl chloride or anhydride and DMSO, methanesulfonyl chloride and DMSO or tetrahydrothiaphene-S-oxide, toluenesulfonyl bromide and DMSO, trifluoromethanesulfonyl anhydride (triflic anhydride) and DMSO, phosphorus pentachloride and DMSO, dimethylphosphoryl chloride and DMSO and isobutylchloroformate and DMSO. The oxidation conditions reported by Reetz et al [*Angew Chem.,* 99, p. 1186, (1987)], *Angew Chem. Int. Ed. Engl.,* 26, p. 1141, 1987) employed oxalyl chloride and DMSO at −78° C.

The preferred oxidation method described in this invention is sulfur trioxide pyridine complex, triethylamine and DMSO at room temperature. This system provides excellent yields of the desired chiral protected amino aldehyde usable without the need for purification i.e., the need to purify kilograms of intermediates by chromatography is eliminated and large scale operations are made less hazardous. Reaction at room temperature also eliminated the need for the use of low temperature reactor which makes the process more suitable for commercial production.

The reaction may be carried out under an inert atmosphere such as nitrogen or argon, or normal or dry air, under atmospheric pressure or in a sealed reaction vessel under positive pressure. Preferred is a nitrogen atmosphere. Alternative amine bases include, for example, tri-butyl amine, tri-isopropyl amine, N-methylpiperidine, N-methyl morpholine, azabicyclononane, diisopropylethylamine, 2,2, 6,6-tetramethylpiperidine, N,N-dimethylaminopyridine, or mixtures of these bases. Triethylamine is a preferred base. Alternatives to pure DMSO as solvent include mixtures of DMSO with non-protic or halogenated solvents such as tetrahydrofuran, ethyl acetate, toluene, xylene, dichloromethane, ethylene dichloride and the like. Dipolar aprotic co-solvents include acetonitrile, dimethylformamide, dimethylacetamide, acetamide, tetramethyl urea and its cyclic analog, N-methylpyrrolidone, sulfolane and the like. Rather than N,N-dibenzylphenylalaninol as the aldehyde precursor, the phenylalaninol derivatives discussed above can be used to provide the corresponding N-monosubstituted [either $P^1$ or $P^2$=H] or N,N-disubstituted aldehyde.

In addition, hydride reduction of an amide or ester derivative of the corresponding alkyl, benzyl or cycloalkenyl nitrogen protected phenylalanine, substituted phenylalanine or cycloalkyl analog of phenyalanine derivative can be carried out to provide a compound of Formula III. Hydride transfer is an additional method of aldehyde synthesis under conditions where aldehyde condensations are avoided, cf, Oppenauer Oxidation.

The aldehydes of this process can also be prepared by methods of reducing protected phenylalanine and phenylalanine analogs or their amide or ester derivatives by, e.g., sodium amalgam with HCl in ethanol or lithium or sodium or potassium or calcium in ammonia. The reaction temperature may be from about −20° C. to about 45° C., and preferably from abut 5° C. to about 25° C. Two additional methods of obtaining the nitrogen protected aldehyde include oxidation of the corresponding alcohol with bleach in the presence of a catalytic amount of 2,2,6,6-tetramethyl-1-pyridyloxy free radical. In a second method, oxidation of the alcohol to the aldehyde is accomplished by a catalytic amount of tetrapropylammonium perruthenate in the presence of N-methylmorpholine-N-oxide.

Alternatively, an acid chloride derivative of a protected phenylalanine or phenylalanine derivative as disclosed above can be reduced with hydrogen and a catalyst such as Pd on barium carbonate or barium sulphate, with or without an additional catalyst moderating agent such as sulfur or a thiol (Rosenmund Reduction).

An important aspect of the present invention is a reaction involving the addition of chloromethyllithium or bromomethyllithium to the α-amino aldehyde. Although addition of chloromethyllithium or bromomethyllithium to aldehydes is known, the addition of such species to racemic or chiral amino aldehydes to form aminoepoxides of the formula

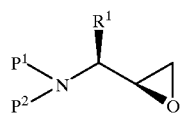

(IV)

is novel. The addition of chloromethyllithium or bromomethyllithium to a chiral amino aldehyde with appropriate amino protecting groups is highly diastereoselective. Preferably, the chloromethyllithium or bromomethyllithium is generated in-situ from the reaction of the dihalomethane and n-butyl lithium. Acceptable methyleneating halomethanes include chloroiodomethane, bromochloromethane, dibromomethane, diiodomethane, bromofluoromethane and the like. The sulfonate ester of the addition product of, for example, hydrogen bromide to formaldehyde is also a methyleneating agent. Tetrahydrofuran is the preferred solvent, however alternative solvents such as toluene, dimethoxyethane, ethylene dichloride, methylene chloride can be used as pure solvents or as a mixture. Dipolar aprotic solvents such as acetonitrile, DMF, N-methylpyrrolidone are useful as solvents or as part of a solvent mixture. The reaction can be carried out under an inert atmosphere such as nitrogen or argon. Other organometallic reagents can be substituted for n-butyl lithium, such as methyl lithium, tert-butyl lithium, sec-butyl lithium, phenyl lithium, phenyl sodium, lithium diisopropylamide, lithium bis (trimethylsilyl)amide, other amide bases, and the like. The reaction can be carried out at temperatures of between about −80° C. to 0° C. but preferably between about −80° C. to −20° C. The most preferred reaction temperatures are between −40° C. to −15° C. Reagents can be added singly but multiple additions are preferred in certain conditions. The preferred pressure of the reaction is atmospheric however a positive pressure is valuable under certain conditions such as a high humidity environment.

Alternative methods of conversion to the epoxides of this invention include substitution of other charged methylenation precursor species followed by their treatment with base to form the analogous anion. Examples of these species include trimethylsulfoxonium tosylate or triflate, tetramethylammonium halide, methyldiphenylsulfoxonium halide wherein halide is chloride, bromide or iodide.

The conversion of the aldehydes of this invention into their epoxide derivative can also be carried out in multiple steps. For example, the addition of the anion of thioanisole prepared from, for example, a butyl or aryl lithium reagent, to the protected aminoaldehyde, oxidation of the resulting protected aminosulfide alcohol with well known oxidizing agents such as hydrogen peroxide, tert-butyl hypochlorite, bleach or sodium periodate to give a sulfoxide. Alkylation of the sulfoxide with, for example, methyl iodide or bromide, methyl tosylate, methyl mesylate, methyl triflate, ethyl bromide, isopropyl bromide, benzyl chloride or the like, in the presence of an organic or inorganic base Alternatively, the protected aminosulfide alcohol can be alkylated with, for example, the alkylating agents above, to provide a sulfonium salts that are subsequently converted into the subject epoxides with tert-amine or mineral bases.

The desired epoxides form, using most preferred conditions, diastereoselectively in ratio amounts of at least about an 85:15 ratio (S:R). The product can be purified by chromatography to give the diastereomerically and enantiomerically pure product but it is more conveniently used directly without purification to prepare HIV protease inhibitors.

The epoxide is then reacted, in a suitable solvent system, with an equal amount, or preferably an excess of, with $R^3NH_2$ to form the amino alcohol of Formula I

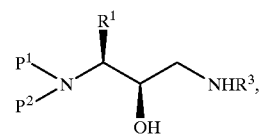

(I)

wherein $R^3$ is as defined above.

The reaction can be conducted over a wide range of temperatures, e.g., from about 10° C. to about 100° C., but is preferably, but not necessarily, conducted at a temperature at which the solvent begins to reflux. Suitable solvent systems include those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. Exemplary amines corresponding to the formula $R^3NH_2$ include benzylamine, isobutylamine, n-butyl amine, isopentylamine, isoamylamine, cyclohexylmethylamine, cyclopentylmethylamine, naphthylmethylamine and the like. In some cases, $R^3NH_2$ can be used as the solvent, such as iso-butylamine.

Alternatively, the protected amino aldehyde of Formula III can also be reacted with a cyanide salt, such as sodium cyanide or potassium cyanide to form a chiral cyanohydrin of the formula

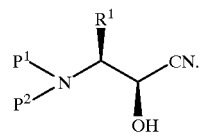

Preferably, a reaction rate enhancer, such as sodium bisulfite, is used to enhance the rate of cyanohydrin formation. Alternatively, trimethylsilylnitrile can be used to form a trimethylsilyloxycyano intermediate, which can be readily hydrolyzed to the cyanohydrin.

The reaction can be carried out at temperatures of between about −5° C. to 5° C. but preferably between about 0° C. to 5° C. The desired cyanohydrins form, using sodium cyanide and sodium bisulfite, diastereoselectively in ratio amounts of at least about an 88:12 ratio (S:R). The product can be purified by chromatography to give the diastereomerically and enantiomerically pure product.

The cyano group can be reduced to the amine of Formula V

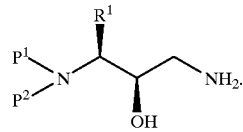

(V)

The reduction can be accomplished using a variety of reducing reagents, such as hydride transfer, metal reductions and catalytic hydrogenation which are well known to those skilled in the art. Examples of hydride reagents with and without heavy metal(s) or heavy metal salts as adjunct reagents include, for example, lithium aluminum hydride, lithium tri-tert-butoxyaluminum hydride, lithium trimethoxy-aluminum hydride, aluminum hydride, diborane (or borane), borane/THF, borane/dimethyl sulfide, borane/pyridine, sodium borohydride, lithium borohydride, sodium borohydride/cobalt salts, sodium borohydride/Raney-nickel, sodium borohydride/acetic acid and the like. Solvents for the reaction include, for the more reactive hydrides, THF, diethyl ether, dimethoxy ethane, diglyme, toluene, heptane, cyclohexane, methyl tert-butyl ether and the like. Solvents or solvent mixtures for reductions using reagents such as sodium borohydride, in addition to the non-protic solvents listed above, can include ethanol, n-butanol, tert-butyl alcohol, ethylene glycol and the like. Metal reductions include, for example, sodium and ethanol. Reaction temperatures can vary between solvent reflux and −20° C. An inert atmosphere such as nitrogen or argon is usually preferred especially where the possibility of flammable gas or solvent production/evolution is possible. Catalytic hydrogenation (metal catalyst plus hydrogen gas) can be carried out in the same solvents as above with metals or metal salts such a nickel, palladium chloride, platinum, rhodium, platinum oxide or palladium on carbon or other catalysts known to those skilled in the art. These catalysts can also be modified with, for example, phosphine ligands, sulfur or sulfur containing compounds or amines such as quinoline. Hydrogenations can be carried out at atmospheric pressure or at elevated pressures to about 1500 psi at temperatures between 0° to about 250° C. The most preferred reducing reagent is diborane·tetrahydrofuran, preferably at room temperature under an atmosphere of nitrogen and atmospheric pressure.

The amine of Formula V can then be reacted with $R^3L$, wherein L is a leaving group selected from halo, tosylate, mesolate and the like, and $R^3$ represents alkyl, alkenyl, alkynyl, hydroxyalkyl, alkoxyalkyl, cycloalkyl, cycloalkylalkyl, heterocycloalkyl, heterocycloalkylalkyl, aralkyl or heteroaralkyl. Alternatively, the primary amino group of Formula V can be reductively alkylated with an aldehyde to introduce the R3 group. For example, when R3 is an isobutyl group, treatment of Formula V with isobutyraldehyde under reductive amination conditions affords the desired Formula I. Similarly, when R3 is an isoamyl group, treatment of Formula V with isovaleraldehyde under reductive amination conditions affords the desired Formula I. Other aldehydes can be used to introduce various R3 groups. Reductive amination can be performed using a variety of reaction conditions well-known to those skilled in the art. For example, the reductive amination of Formula V with an aldehyde can be carried out with a reducing agent such as sodium cyanoborohydride or sodium borohydride in a suitable solvent, such as methanol, ethanol, tetrahydrofuran and the like. Alternatively, the reductive amination can be carried out using hydrogen in the presence of a catalyst such as palladium or platinum, palladium on carbon or platinum on carbon, or various other metal catalysts known to those skilled in the art, in a suitable solvent such as methanol, ethanol, tetrahydrofuran, ethyl acetate, toluene and the like.

Alternatively, the amine of Formula I can be prepared by reduction of the protected amino acid of formula

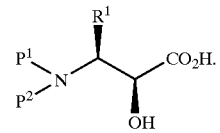

(commercially available from Nippon Kayaku, Japan) to the corresponding alcohol of formula

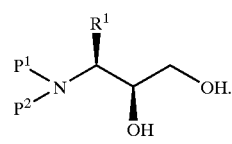

The reduction can be accomplished using a variety of reducing reagents and conditions. A preferred reducing reagent is diborane·tetrahydrofuran. The alcohol is then converted into a leaving group (L') by tosylation, mesylation or conversion into a halo group, such as chloro or bromo:

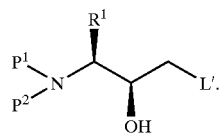

Finally, the leaving group (L') is reacted with $R^3NH_2$ as described above to form amino alcohol of Formula I. Alternatively, base treatment of the alcohol can result in the formation of the amino epoxide of Formula IV.

The above preparation of amino alcohol of Formula I is applicable to mixtures of optical isomers as well as resolved compounds. If a particular optical isomer is desired, it can be selected by the choice of starting material, e.g., L-phenylalanine, D-phenylalanine, L-phenylalaninol, D-phenylalaninol, D-hexahydrophenyl alaninol and the like, or resolution can occur at intermediate or final steps. Chiral auxiliaries such as one or two equivalents of camphor sulfonic acid, citric acid, camphoric acid, 2-methoxyphenylacetic acid and the like can be used to form salts, esters or amides of the compounds of this invention. These compounds or derivatives can be crystallized or separated chromatographically using either a chiral or achiral column as is well known to those skilled in the art.

A further advantage of the present process is that materials can be carried through the above steps without purification of the intermediate products. However, if purification is desired, the intermediates disclosed can be prepared and stored in a pure state.

The practical and efficient synthesis described here has been successfully scaled up to prepare large quantity of intermediates for the preparation of HIV protease inhibitors. It offers several advantages for multikilogram preparations: (1) it does not require the use of hazardous reagents such as diazomethane, (2) it requires no purification by chromatography, (3) it is short and efficient, (4) it utilizes inexpensive and readily available commercial reagents, (5) it produces enantiomerically pure alpha amino epoxides. In particular, the process of the invention produces enantiomerically-pure epoxide as required for the preparation of enantiomerically-pure intermediate for further synthesis of HIV protease inhibitors.

The amino epoxides were prepared utilizing the following procedure as disclosed in Scheme II below.

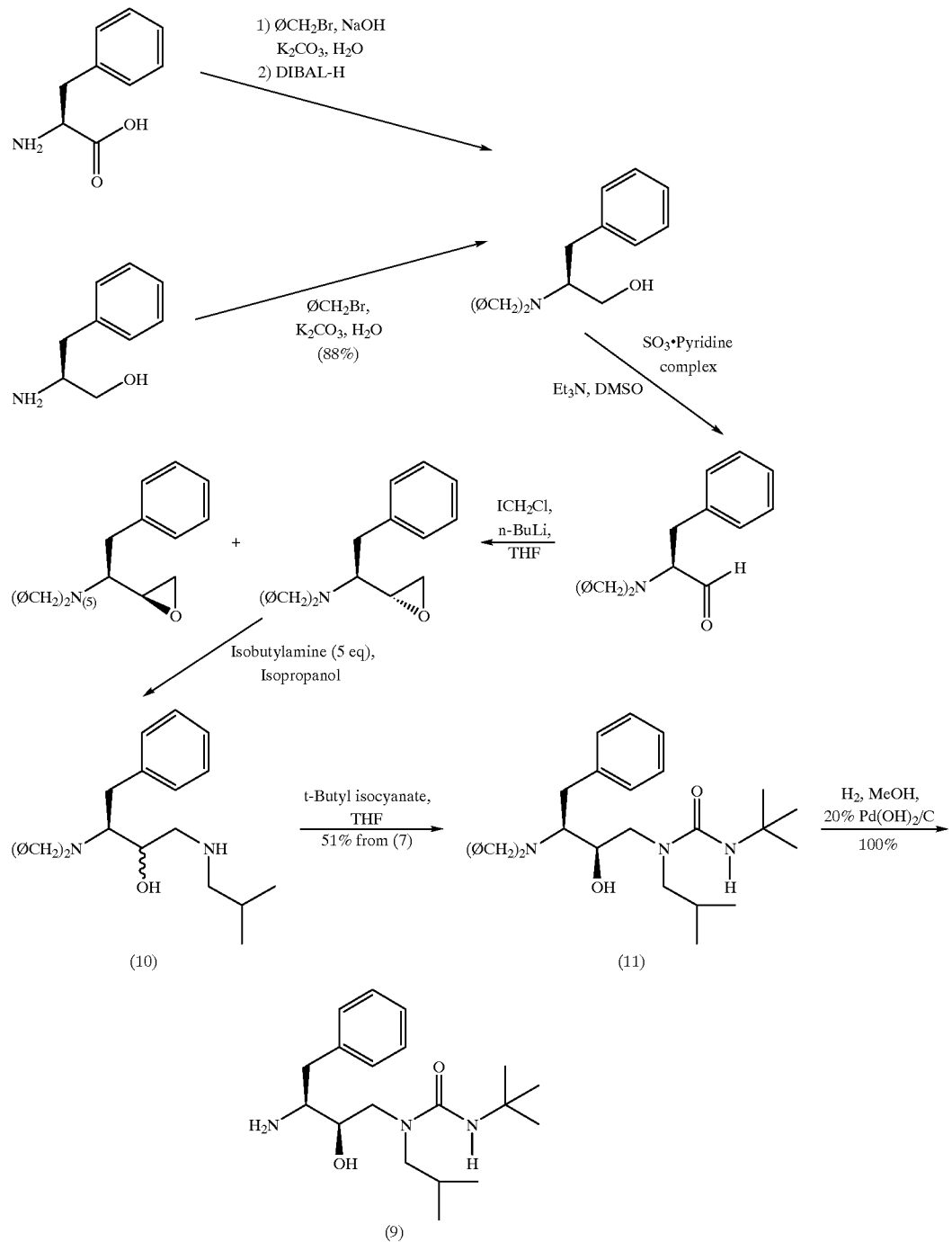

In Scheme II, there is shown a synthesis for the epoxide, chiral N, N,α-S-tris(phenylmethyl)-2S-oxiranemethanamine. The synthesis starts from L-phenylalanine. The aldehyde is prepared in three steps from L-phenylalanine or phenylalaninol. L-Phenylalanine is converted to the N,N-dibenzylamino acid benzyl ester using benzyl bromide under aqueous conditions. The reduction of benzyl ester is carried out using diisobutylaluminum hydride (DIBAL-H) in toluene. Alternatively, lithium aluminum hydride may be used. Instead of purification by chromatography, the product is purified by an acid (hydrochloric acid) quench of the reaction, the hydrochloride salt is filtered off as a white solid and then liberated by an acid/base extraction. After one recrystallization, chemically and optically pure alcohol is obtained. Alternately, and preferably, the alcohol can be obtained in one step in 88% yield by the benzylation of L-phenylalaninol using benzylbromide under aqueous conditions. The oxidation of alcohol to aldehyde is also modified to allow for more convenient operation during scaleup. Instead of the standard Swern procedures using oxalyl chloride and DMSO in methylene chloride at low temperatures (very exothermic reaction), sulfur trioxide-pyridine/DMSO was employed (Parikh, J., Doering, W., *J. Am. Chem. Soc.*, 89, p. 5505, 1967) which can be conveniently performed at room temperature to give excellent yields of the desired aldehyde with high chemical and enantiomer purity which does not require purification.

An important reaction involves the addition of chloromethyllithium or bromomethyllithium to the aldehyde. Although addition of chloromethyllithium or bromomethyllithium to aldehydes has been reported previously, the addition of such species to chiral α-amino aldehydes to form chiral-aminoepoxides is believed to be novel. Now, chloromethyllithium or bromomethyllithium is generated in-situ from chloroiodomethane(or bromochloromethane) or dibromomethane and n-butyl lithium at a temperature in a range from about −78° C. to about −10° C. in THF in the presence of aldehyde. The desired chlorohydrin or bromohydrin is formed as evidenced by TLC analyses. After warming to room temperature, the desired epoxide is formed diastereoselectively in a 85:15 ratio (S:R). The product can be purified by chromatography to give the diastereomerically pure product as a colorless oil but it is more conveniently used directly without purification.

Scheme III illustrates the preparation of the aminopropylurea (9) utilizing mixed protected amine of phenylalaninol, where BOC is t-butoxycarbonyl and Bn is benzyl.

Scheme III

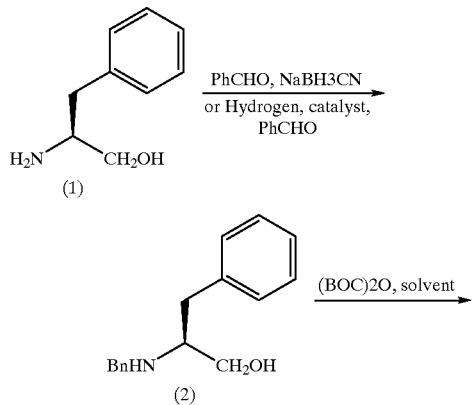

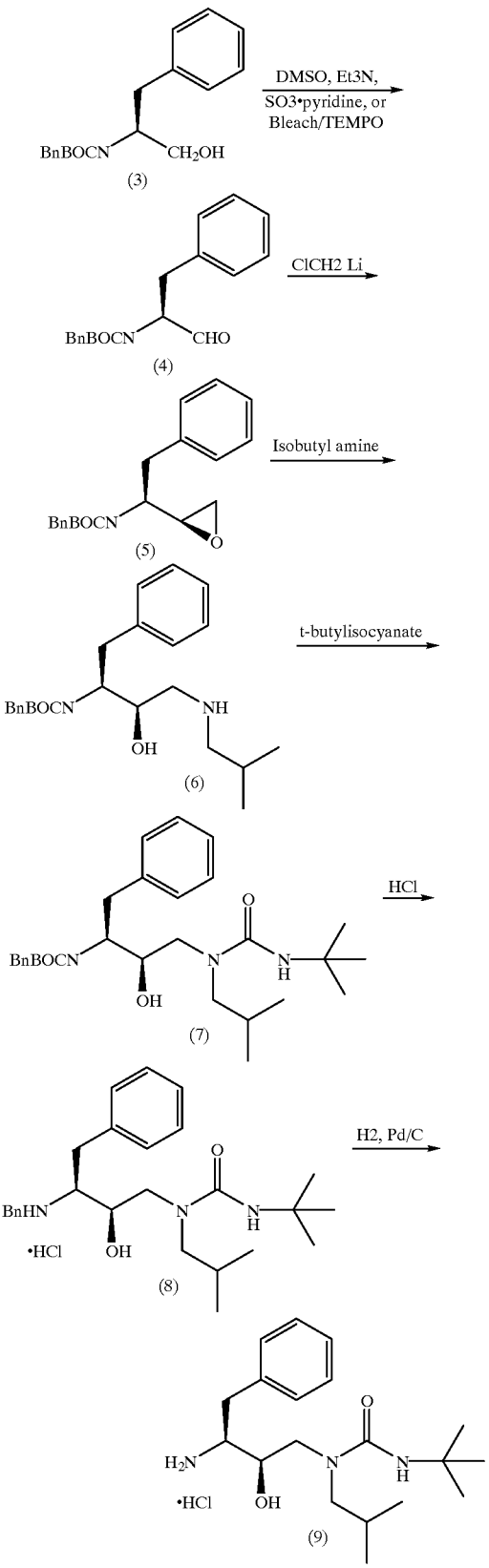

Scheme IV illustrates an alternative preparation of the amino epoxide (5) utilizing a sulfur ylide.

Scheme IV
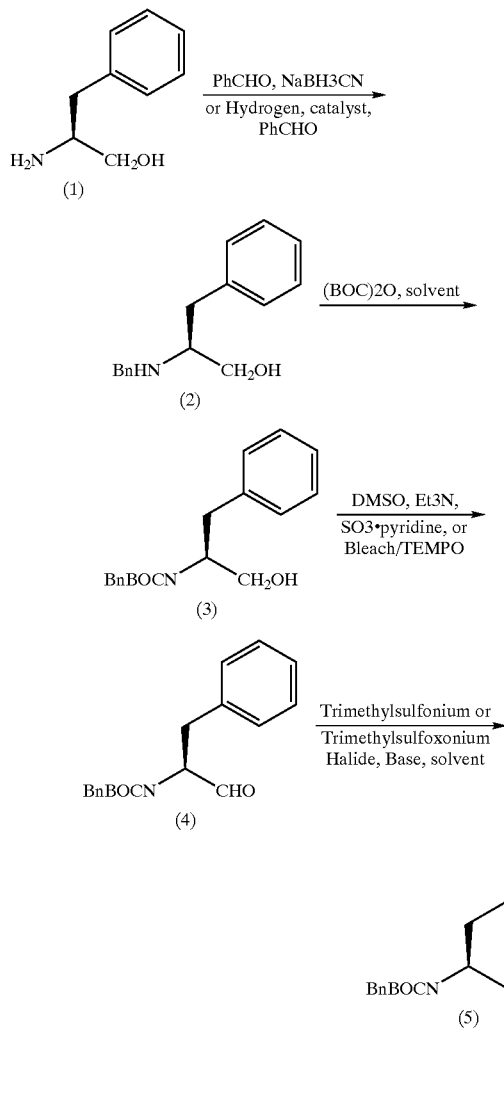
The aminopropylurea (9) was also prepared utilizing the procedure as disclosed in Scheme V below.
Scheme V
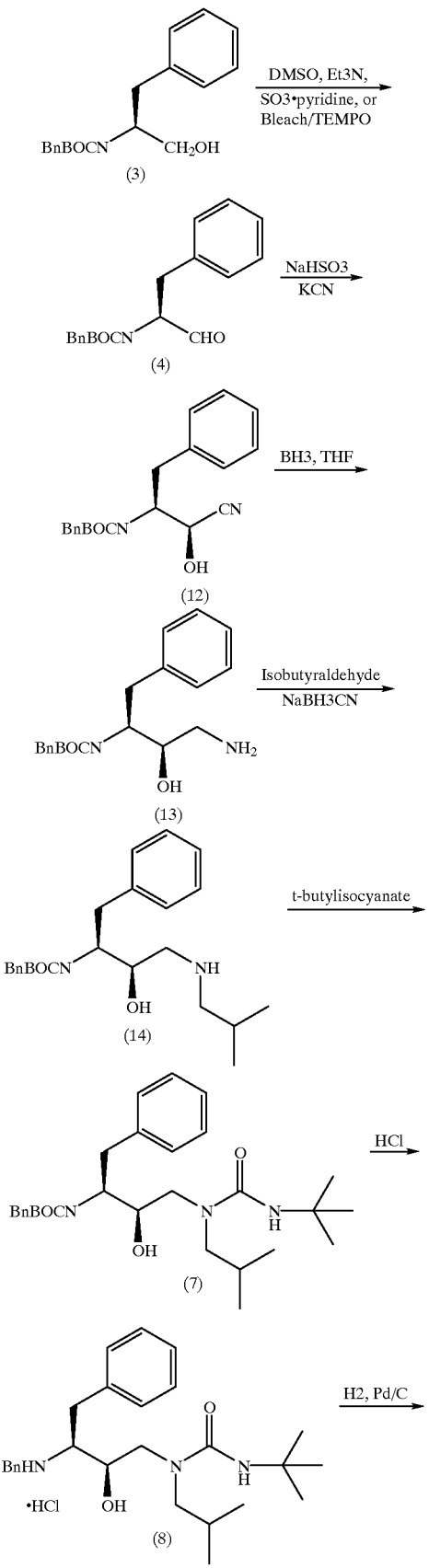

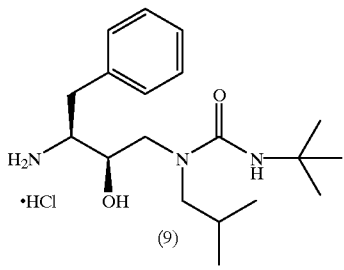

(9)

In Scheme V a mixed protected amine of phenylalaninal, where BOC is t-butoxycarbonyl and Bn is benzyl, was reacted with potassium cyanide to form the desired stereoisomeric cyanohydrin (12) in high yield. In additional to the stereospecificity of the cyanohydrin reaction, this process has the added advantage of being easier and less expensive because the temperature of the reactions need not be less than −5° C.

The aminourea (9) was also prepared utilizing the procedure as disclosed in Scheme VI below.

Scheme VI

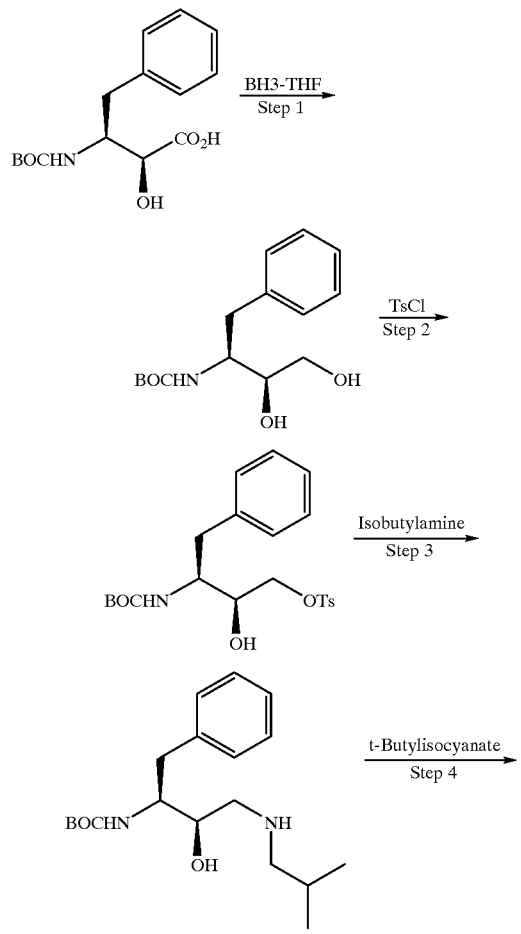

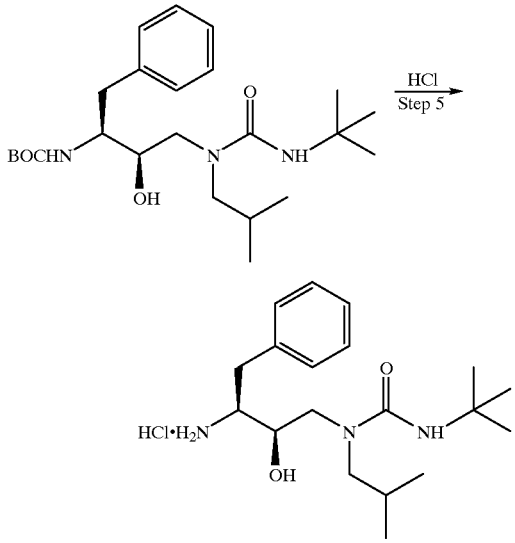

The procedure in Scheme VI required only one protecting group, BOC, for the amine of the hydroxyamino acid. This procedure has the advantage of having the desired stereochemistry of the benzyl and hydroxy groups established in the starting material. Thus the chirality does not need to be introduced with the resulting loss of material due to preparation of diastereomers.

EXAMPLE 1

β-2-[Bis(phenylmethyl)amino]benzenepropanol

METHOD 1: βS-2-[Bis(phenylmethyl)amino] benzenepropanol from the DIBAL Reduction of N,N-bis (phenylmethyl)-L-Phenylalanine phenylmethyl ester Step 1:

A solution of L-phenylalanine (50.0 g, 0.302 mol), sodium hydroxide (24.2 g, 0.605 mol) and potassium carbonate (83.6 g, 0.605 mol) in water (500 mL) was heated to 97° C. Benzyl bromide (108.5 mL, 0.605 mol) was then slowly added (addition time—25 min). The mixture was stirred at 97° C. for 30 minutes under a nitrogen atmosphere. The solution was cooled to room temperature and extracted with toluene (2×250 mL). The combined organic layers were washed with water and brine, dried over magnesium sulfate, filtered and concentrated to an oil. The identity of the product was confirmed as follows. Analytical TLC (10% ethyl acetate/hexane, silica gel) showed major component at Rf value=0.32 to be the desired tribenzylated compound, N,N-bis(phenylmethyl)-L-phenylalanine phenylmethyl ester. This compound can be purified by column chromatography (silica gel, 15% ethyl acetate/hexane). Usually the product is pure enough to be used directly in the next step without further purification. $^1$H NMR spectrum was in agreement with published literature. $^1$H NMR (CDCL$_3$) ∂, 3.00 and 3.14 (ABX-system, 2H, $J_{AB}$=14.1 Hz, $J_{AX}$=7.3 Hz and $J_{BX}$=5.9 Hz), 3.54 and 3.92 (AB-System, 4 H, $J_{AB}$=13.9 Hz), 3.71 (t, 1H, J=7.6 Hz), 5.11 and 5.23 (AB-System, 2H, $J_{AB}$=12.3 Hz), and 7.18 (m, 20 H). EIMS: m/z 434 (M−1).

Step 2:

The benzylated phenylalanine phenylmethyl ester (0.302 mol) from the previous reaction was dissolved in toluene (750 mL) and cooled to −55° C. A 1.5 M solution of DIBAL in toluene (443.9 mL, 0.666 mol) was added at a rate to maintain the temperature between −55 to −50° C. (addition time—1 hr). The mixture was stirred for 20 minutes under a nitrogen atmosphere and then quenched at −55° C. by the slow addition of methanol (37 ml). The cold solution was then poured into cold (5° C.) 1.5 N HCl solution (1.8 L). The precipitated solid (approx. 138 g) was filtered off and washed with toluene. The solid material was suspended in a mixture of toluene (400 mL) and water (100 ml). The mixture was cooled to 5° C. and treated with 2.5 N NaOH (186 mL) and then stirred at room temperature until solid dissolved. The toluene layer was separated from the aqueous phase and washed with water and brine, dried over magnesium sulfate, filtered and concentrated to a volume of 75 mL (89 g). Ethyl acetate (25 mL) and hexane (25 mL) were added to the residue upon which the desired alcohol product began to crystallize. After 30 min, an additional 50 mL hexane were added to promote further crystallization. The solid was filtered off and washed with 50 mL hexane to give 34.9 g of first crop product. A second crop of product (5.6 g) was isolated by refiltering the mother liquor. The two crops were combined and recrystallized from ethyl acetate (20 mL) and hexane (30 mL) to give 40 g of βS-2-[Bis (phenyl-methyl)amino]benzenepropanol, 40% yield from L-phenylalanine. An additional 7 g (7%) of product can be obtained from recrystallization of the concentrated mother liquor. TLC of product Rf=0.23 (10% ethyl acetate/hexane, silica gel); $^1$H NMR (CDCl$_3$) ∂ 2.44 (m, 1 H,), 3.09 (m, 2H), 3.33 (m, 1H), 3.48 and 3.92 (AB-System, 4H, $J_{AB}$=13.3 Hz), 3.52 (m, 1H) and 7.23 (m, 15H); [α]$_D$25 +42.4 (c 1.45, CH$_2$Cl$_2$) ; DSC 77.67° C.; Anal. Calcd. for C$_{23}$H$_{25}$ON: C, 83.34; H, 7.60; N, 4.23. Found: C, 83.43; H, 7.59; N, 4.22. HPLC on chiral stationary phase: Cyclobond I SP column (250×4.6 mm I.D.), mobile phase: methanol/triethyl ammonium acetate buffer pH 4.2 (58:42, v/v), flow-rate of 0.5 ml/min, detection with detector at 230 nm and a temperature of 0° C. Retention time: 11.25 min., retention time of the desired product enantiomer: 12.5 min.

METHOD 2: Preparation of βS-2-[Bis(phenylmethyl) amino]benzene-propanol from the N,N-Dibenzylation of L-Phenylalaninol L-phenylalaninol (176.6 g, 1.168 mol) was added to a stirred solution of potassium carbonate (484.6 g, 3.506 mol) in 710 mL of water. The mixture was heated to 65° C. under a nitrogen atmosphere. A solution of benzyl bromide (400 g, 2.339 mol) in 3A ethanol (305 mL) was added at a rate that maintained the temperature between 60–68° C. The biphasic solution was stirred at 65° C. for 55 min and then allowed to cool to 10° C. with vigorous stirring. The oily product solidified into small granules. The product was diluted with 2.0 L of tap water and stirred for 5 minutes to dissolve the inorganic by products. The product was isolated by filtration under reduced pressure and washed with water until the pH is 7. The crude product obtained was air dried overnight to give a semi-dry solid (407 g) which was recrystallized from 1.1 L of ethyl acetate/heptane (1:10 by volume). The product was isolated by filtration (at −8° C.), washed with 1.6 L of cold (−10° C. ) ethyl acetate/heptane (1:10 by volume) and air-dried to give 339 g (88% yield) of βS-2-[Bis (phenylmethyl)amino]benzene-propanol, Mp=71.5–73.0° C. More product can be obtained from the mother liquor if necessary. The other analytical characterization was identical to compound prepared as described in Method 1.

EXAMPLE 2

αS-[Bis(phenylmethyl)amino] benzenepropanaldehyde

METHOD 1:

βS-2-[Bis(phenylmethyl)amino]benzene-propanol (200 g, 0.604 mol) was dissolved in triethylamine (300 mL, 2.15 mol). The mixture was cooled to 12° C. and a solution of sulfur trioxide/pyridine complex (380 g, 2.39 mol) in DMSO (1.6 L) was added at a rate to maintain the temperature between 8–17° C. (addition time—1.0 h). The solution was stirred at ambient temperature under a nitrogen atmosphere for 1.5 hour at which time the reaction was complete by TLC analysis (33% ethyl acetate/hexane, silica gel). The reaction mixture was cooled with ice water and quenched with 1.6 L of cold water (10–15° C.) over 45 minutes. The resultant solution was extracted with ethyl acetate (2.0 L), washed with 5% citric acid (2.0 L), and brine (2.2 L), dried over MgSO$_4$ (280 g) and filtered. The solvent was removed on a rotary evaporator at 35–40° C. and then dried under vacuum to give 198.8 g of αS-[Bis-(phenylmethyl)amino]-benzenepropanaldehyde as a pale yellow oil (99.9%). The crude product obtained was pure enough to be used directly in the next step without purification. The analytical data of the compound were consistent with the published literature. [α]$_D$25=−92.9° (c 1.87, CH$_2$Cl$_2$); $^1$H NMR (400 MHz, CDCl$_3$) ∂, 2.94 and 3.15 (ABX-System, 2H, $J_{AB}$=13.9 Hz, $J_{AX}$=7.3 Hz and $J_{BX}$=6.2 Hz), 3.56 (t, 1H, 7.1 Hz), 3.69 and 3.82 (AB-System, 4H, $J_{AB}$=13.7 Hz), 7.25 (m, 15 H) and 9.72 (s, 1H); HRMS Calcd for (M+1) C$_{23}$H$_{24}$NO 330.450, found: 330.1836. Anal. Calcd. for C$_{23}$H$_{23}$ON: C, 83.86; H, 7.04; N, 4.25. Found: C, 83.64; H, 7.42; N, 4.19. HPLC on chiral stationary phase:(S,S) Pirkle-Whelk-O 1 column (250×4.6 mm I.D.), mobile phase: hexane/isopropanol (99.5:0.5, v/v), flow-rate: 1.5 ml/min, detection with UV detector at 210 nm. Retention time of the desired S-isomer: 8.75 min., retention time of the R-enantiomer 10.62 min.

METHOD 2:

A solution of oxalyl chloride (8.4 ml, 0.096 mol) in dichloromethane (240 ml) was cooled to −74° C. A solution of DMSO (12.0 ml, 0.155 mol) in dichloromethane (50 ml) was then slowly added at a rate to maintain the temperature at −74° C. (addition time ~1.25 hr). The mixture was stirred for 5 min. followed by addition of a solution of βS-2-[bis (phenylmethyl)amino]benzene-propanol (0.074 mol) in 100 ml of dichloromethane (addition time −20 min., temp. −75° C. to −68° C.). The solution was stirred at −78° C. for 35 minutes under a nitrogen atmosphere. Triethylamine (41.2 ml, 0.295 mol) was then added over 10 min. (temp. −78° to −68° C.) upon which the ammonium salt precipitated. The cold mixture was stirred for 30 min. and then water (225 ml) was added. The dichloromethane layer was separated from the aqueous phase and washed with water, brine, dried over magnesium sulfate, filtered and concentrated. The residue was diluted with ethyl acetate and hexane and then filtered to further remove the ammonium salt. The filtrate was concentrated to give αS-[bis(phenylmethyl)amino] benzenepropanaldehyde. The aldehyde was carried on to the next step without purification.

METHOD 3:

To a mixture of 1.0 g (3.0 mmoles) of βS-2-[bis (phenylmethyl)amino]benzenepropanol 0.531 g (4.53 mmoles) of N-methyl morpholine, 2.27 g of molecular sieves(4A) and 9.1 mL of acetonitrile was added 53 mg (0.15 mmoles) of tetrapropylammonium perruthenate (TPAP). The mixture was stirred for 40 minutes at room temperature and concentrated under reduced pressure. The residue was suspended in 15 mL of ethyl acetate, filtered through a pad of silica gel. The filtrate was concentrated under reduced pressure to give a product containing approximately 50% of αS-2-[bis(phenylmethyl)amino]benzene propanaldehyde as a pale yellow oil.

METHOD 4:

To a solution of 1.0 g (3.02 mmoles) of βS-2-[bis (phenylmethyl)amino]benzenepropanol in 9.0 mL of toluene was added 4.69 mg (0.03 mmoles) of 2,2,6,6-tetramethyl-1-peridinyloxy, free radical (TEMPO), 0.32 g (3.11 mmoles) of sodium bromide, 9.0 mL of ethyl acetate and 1.5 mL of water. The mixture was cooled to 0° C. and an aqueous solution of 2.87 mL of 5% household bleach containing 0.735 g (8.75 mmoles) of sodium bicarbonate and 8.53 mL of water was added slowly over 25 minutes. The mixture was stirred at 0° C. for 60 minutes. Two more additions (1.44 mL each) of bleach was added followed by stirring for 10 minutes. The two phase mixture was allowed to separate. The aqueous layer was extracted twice with 20 mL of ethyl acetate. The combined organic layer was washed with 4.0 mL of a solution containing 25 mg of potassium iodide and water(4.0 mL), 20 mL of 10% aqueous sodium thiosulfate solution and then brine solution. The organic solution was dried over magnesium sulfate, filtered and concentrated under reduced pressure to give 1.34 g of crude oil containing a small amount of the desired product aldehyde, αS-[bis (phenylmethyl)amino]benzenepropanaldehyde.

METHOD 5:

Following the same procedures as described in Example 2 (Method 1) except 3.0 equivalents of sulfur trioxide pyridine complex was used and αS-[bis(phenylmethyl) amino]benzenepropanaldehyde was isolated in comparable yields.

EXAMPLE 3

N,N, αS-Tris(phenylmethyl)-2S-oxiranemethanamine

METHOD 1:

A solution of αS-[Bis(phenylmethyl)amino] benzenepropanaldehyde (191.7 g, 0.58 mol) and chloroiodomethane (56.4 mL, 0.77 mol) in tetrahydrofuran (1.8 L) was cooled to −30 to −35° C. (colder temperature such as −70° C. also worked well but warmer temperatures are more readily achieved in large scale operations) in a stainless steel reactor under a nitrogen atmosphere. A solution of n-butyl lithium in hexane (1.6 M, 365 mL, 0.58 mol) was then added at a rate that maintained the temperature below −25° C. After addition the mixture was stirred at −30 to −35° C. for 10 minutes. More additions of reagents were carried out in the following manner: (1) additional chloroiodomethane (17 mL) was added, followed by n-butyl lithium (110 mL) at <−25° C. After addition the mixture was stirred at −30 to −35° C. for 10 minutes. This was repeated once. (2) Additional chloroiodomethane (8.5 mL, 0.11 mol) was added, followed by n-butyl lithium (55 mL, 0.088 mol) at <−25° C. After addition the mixture was stirred at −30 to −35° C. for 10 minutes. This was repeated 5 times. (3) Additional chloroiodomethane (8.5 mL, 0.11 mol) was added, followed by n-butyl lithium (37 mL, 0.059 mol) at <−25° C. After addition the mixture was stirred at −30 to −35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material. (The crude product weight was >100%. Due to the relative instability of the product on silica gel, the crude product is usually used directly in the next step without purification). The diastereomeric ratio of the crude mixture was determined by proton NMR: (2S)/(2R): 86:14. The minor and major epoxide diastereomers were characterized in this mixture by tlc analysis (silica gel, 10% ethyl acetate/hexane), Rf=0.29 & 0.32, respectively. An analytical sample of each of the diastereomers was obtained by purification on silica-gel chromatography (3% ethyl acetate/hexane) and characterized as follows:

N,N, αS-Tris(phenylmethyl)-2S-oxiranemethanamine $^1$H NMR (400 MHz, CDCl$_3$) ∂ 2.49 and 2.51 (AB-System, 1H, J$_{AB}$=2.82), 2.76 and 2.77 (AB-System, 1H, J$_{AB}$=4.03), 2.83 (m, 2H), 2.99 & 3.03 (AB-system, 1H, J$_{AB}$=10.1 Hz), 3.15 (m, 1H), 3.73 & 3.84 (AB-System, 4H, J$_{AB}$=14.00), 7.21 (m, 15H); $^{13}$C NMR (400 MHz,CDCl$_3$) ∂ 139.55, 129.45, 128.42, 128.14, 128.09, 126.84, 125.97, 60.32, 54.23, 52.13, 45.99, 33.76; HRMS Calcd for C$_{24}$H$_{26}$NO (M+1) 344.477, found 344.2003.

N,N, αS-Tris(phenylmethyl)-2R-oxiranemethanamine $^1$H NMR (300 MHz, CDCl$_3$) ∂ 2.20 (m, 1H), 2.59 (m, 1H), 2.75 (m, 2H), 2.97 (m, 1H), 3.14 (m, 1H), 3.85 (AB-System, 4H), 7.25 (m, 15H).HPLC on chiral stationary phase: Pirkle-Whelk-O 1 column (250×4.6 mm I.D.), mobile phase: hexane/isopropanol (99.5:0.5, v/v), flow-rate: 1.5 ml/min, detection with UV detector at 210 nm. Retention time of(8): 9.38 min., retention time of enantiomer of (4): 13.75 min.

METHOD 2:

A solution of the crude aldehyde 0.074 mol and chloroiodomethane (7.0 ml, 0.096 mol) in tetrahydrofuran (285 ml) was cooled to −78° C., under a nitrogen atmosphere. A 1.6 M solution of n-butyl lithium in hexane (25 ml, 0.040 mol) was then added at a rate to maintain the temperature at −75° C. (addition time—15 min.). After the first addition, additional chloroiodomethane (1.6 ml, 0.022 mol) was added again, followed by n-butyl lithium (23 ml, 0.037 mol), keeping the temperature at −75° C. The mixture was stirred for 15 min. Each of the reagents, chloroiodomethane (0.70 ml, 0.010 mol) and n-butyl lithium (5 ml, 0.008 mol) were added 4 more times over 45 min. at −75° C. The cooling bath was then removed and the solution warmed to 22° C. over 1.5 hr. The mixture was poured into 300 ml of saturated aq. ammonium chloride solution. The tetrahydrofuran layer was separated. The aqueous phase was extracted with ethyl acetate (1×300 ml). The combined organic layers were washed with brine, dried over magnesium sulfate, filtered and concentrated to give a brown oil (27.4 g). The product could be used in the next step without purification. The desired diastereomer can be purified by recrystallization at a subsequent step. The product could also be purified by chromatography.

METHOD 3:

A solution of αS-[Bis(phenylmethyl)amino] benzenepropanaldehyde (178.84 g, 0.54 mol) and bromochloromethane (46 mL, 0.71 mol) in tetrahydrofuran (1.8 L) was cooled to −30 to −35° C. (colder temperature such as −70° C. also worked well but warmer temperatures are more readily achieved in large scale operations) in a stainless steel reactor under a nitrogen atmosphere. A solution of n-butyl lithium in hexane (1.6 M, 340 mL, 0.54 mol) was then added at a rate that maintained the temperature below −25° C. After addition the mixture was stirred at −30 to −35° C. for 10 minutes. More additions of reagents were carried out in the following manner: (1) additional bromochloromethane (14 mL) was added, followed by n-butyl lithium (102 mL) at <−25° C. After addition the mixture was stirred at −30 to −35° C. for 10 minutes. This was repeated once. (2) Additional bromochloromethane (7 mL, 0.11 mol) was added, followed by n-butyl lithium (51 mL, 0.082 mol) at <−25° C. After addition the mixture was stirred at −30 to −35° C. for 10 minutes. This was repeated 5 times. (3) Additional bromochloromethane (7 mL, 0.11 mol) was added, followed by n-butyl lithium (51 mL, 0.082 mol) at <−25° C. After addition the mixture was stirred at −30 to −35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material.

METHOD 4:

Following the same procedures as described in Example 3 (Method 3) except the reaction temperatures were at −20° C. The resulting N,N,αS-tris(phenylmethyl)-2S-oxiranemethanamine was a diastereomeric mixture of lesser purity then that of Method 3.

METHOD 5:

Following the same procedures as described in Example 3 (Method 3) except the reaction temperatures were at −70−−78° C. The resulting N,N,αS-tris(phenylmethyl)-2S-oxiranemethanamine was a diastereomeric mixture, which was used directly in the subsequent steps without purification.

METHOD 6:

Following the same procedures as described in Example 3 (Method 3) except a continuous addition of bromochloromethane and n-butyl lithium was used at −30 to −35° C. After the reaction and work up procedures as described in Example 3 (Method 3), the desired N,N,αS-tris (phenylmethyl)-2S-oxiranemethanamine was isolated in comparable yields and purities.

METHOD 7:

Following the same procedures as described in Example 3 (Method 2) except dibromomethane was used instead of chloroiodomethane. After the reaction and work up procedures as described in Example 3 (Method 2), the desired N,N,αS-tris(phenylmethyl)-2S-oxirane-methanamine was isolated.

EXAMPLE 4

N-[3 (S)-[N,N-bis(phenylmethyl)amino]-2(R) -hydroxy-4-phenylbutyl]-N-isobutylamine To a solution of crude N,N-dibenzyl-3(S)-amino-1,2(S)-epoxy-4-phenylbutane (388.5 g, 1.13 mol) in isopropanol (2.7 L) (or ethyl acetate) was added isobutylamine (1.7 kgm, 23.1 mol) over 2 min. The temperature increased from 25° C. and to 30° C. The solution was heated to 82° C. and stirred at this temperature for 1.5 h. The warm solution was concentrated under reduced pressure at 65° C. The brown oil residue was transferred to a 3-L flask and dried in vacuo (0.8 mm Hg) for 16 h to give 450 g of 3S-[N,N-bis (phenylmethyl)amino-4-phenylbutan-2R-ol as a crude oil.

An analytical sample of the desired major diastereomeric product was obtained by purifying a small sample of crude product by silica gel chromatography (40% ethyl acetate/ hexane). Tlc analysis: silica gel, 40% ethyl acetate/hexane; Rf=0.28; HPLC analysis: ultrasphere ODS column, 25% triethylamino-/phosphate buffer pH 3-acetonitrile, flow rate 1 mL/min, UV detector; retention time 7.49 min.; HRMS Calcd for $C_{28}H_{27}N_2O$ (M+1) 417.616, found 417.2887. An analytical sample of the minor diastereomeric product, 3S-[N,N-bis(phenylmethyl)amino]1-(2-methylpropyl)amino-4-phenylbutan-2S-ol was also obtained by purifying a small sample of crude product by silica gel chromatography (40% ethyl acetate/hexane).

EXAMPLE 5

N-[3(S)-[N,N-bis(phenylmethyl)amino]-2(R)-hydroxy-4-phenylbutyl]-N-isobutylamine·oxalic acid salt To a solution of oxalic acid (8.08 g, 89.72 mmol) in methanol (76 mL) was added a solution of crude 3(S)-[N, N-bis(phenylmethyl)amino]-1-(2-methylpropyl)amino-4-phenylbutan-2(R)-ol {39.68 g, which contains about 25.44 g (61.06 mmol) of 3(S),2(R) isomer and about 4.49 g (10.78 mmol) of 3(S),2(S) isomer} in ethyl acetate (90 mL) over 15 minutes. The mixture was stirred at room temperature for about 2 hours. Solid was isolated by filtration, washed with ethyl acetate (2×20 mL) and dried in vacuo for about 1 hour to yield 21.86 g (70.7% isomer recovery) of 97% diastereomerically pure salt (based on HPLC peak areas). HPLC analysis: Vydec-peptide/protein C18 column, UV detector 254 nm, flow rate 2 mL/min., gradient {A=0.05% trifluoroacetic acid in water, B=0.05% trifluoroacetic acid in acetonitrile, 0 min. 75% A/25% B, 30 min. 10% A/90% B, 35 min. 10% A/90% B, 37 min. 75% A/25% B}; Retention time 10.68 min. (3(S),2(R) isomer) and 9.73 min. (3(S),2(S) isomer). Mp=174.99° C.; Microanalysis: Calc.: C 71.05%, H 7.50%, N 5.53%; Found: C 71.71%, H 7.75%, N 5.39%.

Alternatively, oxalic acid dihydrate (119 g, 0.94 mole) was added to a 5000 mL round bottom flask fitted with a mechanical stirrer and a dropping funnel. Methanol (1000 ml) was added and the mixture stirred until dissolution was complete. A solution of crude 3(S)-[N,N-bis(phenylmethyl) amino]-1-(2-methylpropyl)amino-4- phenylbutan-2(R)-ol in ethyl acetate (1800 ml, 0.212 g amino alcohol isomers/mL, 0.9160 moles) was added over a twenty minute period. The mixture was stirred for 18 hours and the solid product was isolated by centrifugation in six portions at 400G. Each portion was washed with 125 mL of ethyl acetate. The salt was then collected and dried overnight at 1 torr to yield 336.3 g of product (71% based upon total amino alcohol). HPLC/MS (electrospray) was consistent with the desired product (m/z 417 [M+H]⁺).

Alternatively, crude 3(S)-[N,N-bis(phenylmethyl)amino]-1- (2-methylpropyl)amino-4-phenylbutan-2 (R)-ol (5 g) was dissolved in methyl-tert-butylether (MTBE) (10 mL) and oxalic acid (1 g) in methanol (4 mL) was added. The mixture was stirred for about 2 hours. The resulting solid was filtered, washed with cold MTBE and dried to yield 2.1 g of white solid of about 98.9% diastereomerically pure (based on HPLC peak areas).

EXAMPLE 6

N-[3(S)-[N,N-bis(phenylmethyl)amino]2(R)-hydroxy-4-phenylbutyl]-N-isobutylamine·acetic acid salt To a solution of crude 3(S)-[N,N-bis(phenylmethyl) amino]-1-(2-methylpropyl)amino-4-phenylbutan-2(R)-ol in methyl-tert-butylether (MTBE) (45 mL, 1.1 g amino alcohol isomers/mL) was added acetic acid (6.9 mL) dropwise. The mixture was stirred for about 1 hour at room temperature. The solvent was removed in vacuo to yield a brown oil about 85% diastereomerically pure product (based on HPLC peak areas). The brown oil was crystallized as follows: 0.2 g of the oil was dissolved in the first solvent with heat to obtain a clear solution, the second solvent was added until the solution became cloudy, the mixture was heated again to clarity, seeded with about 99% diastereomerically pure product, cooled to room temperature and then stored in a refrigerator overnight. The crystals were filtered, washed with the second solvent and dried. The diastereomeric purity of the crystals was calculated from the HPLC peak areas. The results are shown in Table 1.

TABLE 1

| First Solvent | Second Solvent | Solvent Ratio | Recovery Weight (g) | Diastereomeric Purity (%) |
|---|---|---|---|---|
| MTBE | Heptane | 1:10 | 0.13 | 98.3 |
| MTBE | Hexane | 1:10 | 0.03 | 99.6 |
| Methanol | Water | 1:1.5 | 0.05 | 99.5 |
| Toluene | Heptane | 1:10 | 0.14 | 98.7 |
| Toluene | Hexane | 1:10 | 0.10 | 99.7 |

Alternatively, crude 3(S)-[N,N-bis(phenylmethyl)amino]-1-(2-methylpropyl)amino-4-phenylbutan-2(R)-ol (50.0 g, which contains about 30.06 g (76.95 mmol) of 3(S),2(R) isomer and about 5.66 g (13.58 mmol) of 3(S),2(S) isomer} was dissolved in methyl-tert-butylether (45.0 mL). To this solution was added acetic acid (6.90 mL, 120.6 mmol) over a period of about 10 min. The mixture was stirred at room temperature for about 1 hour and concentrated under reduced pressure. The oily residue was purified by recrystallization from methyl-tert-butylether (32 mL) and heptane (320 mL). Solid was isolated by filtration, washed with cold heptane and dried in vacuo for about 1 hour to afford 21.34 g (58.2% isomer recovery) of 96% diastereomerically pure monoacetic acid salt (based on HPLC peak areas). Mp=105–106° C.; Microanalysis: Calc.: C 75.53%, H 8.39%, N 5.87%; Found: C 75.05%, H 8.75%, N 5.71%.

EXAMPLE 7

N-[3(S)-[N,N-bis(phenylmethyl)amino]-2(R)-hydroxy-4-phenylbutyl]-N-isobutylamine·L-tartaric acid salt Crude 3(S)-[N,N-bis(phenylmethyl)amino]-1-(2-methylpropyl)amino-4-phenylbutan-2(R)-ol (10.48 g, which contains about 6.72 g (16.13 mmol) of 3(S),2(R) isomer and about 1.19 g (2.85 mmol) of 3(S),2(S) isomer} was dissolved in tetrahydrofuran (10.0 mL). To this solution was added a solution of L-tartaric acid (2.85 g, 19 mmol) in methanol (5.0 mL) over a period of about 5 min. The mixture was stirred at room temperature for about 10 min. and concentrated under reduced pressure. Methyl-tert-butylether (20.0 mL) was added to the oily residue and the mixture was stirred at room temperature for about 1 hour. Solid was isolated by filtration to afford 7.50 g of crude salt. The crude salt was purified by recrystallization from ethyl acetate and heptane at room temperature to yield 4.13 g (45.2% isomer recovery) of 95% diastereomerically pure L-tartaric acid salt (based on HPLC peak areas). Microanalysis: Calc.: C 67.76%, H 7.41%, N 4.94%; Found: C 70.06%, H 7.47%, N 5.07%.

EXAMPLE 8

N-[3(S)-[N,N-bis(phenylmethyl)amino]-2(R)-hydroxy-4-phenylbutyl]-N-isobutylamine·dihydrochloric acid salt Crude 3(S)-[N,N-bis(phenylmethyl) amino]-1-(2-methylpropyl)amino-4-phenylbutan-2(R)-ol (10.0 g, which contains about 6.41 g (15.39 mmol) of 3(S),2(R) isomer and about 1.13 g (2.72 mmol) of 3(S),2(S) isomer} was dissolved in tetrahydrofuran (20.0 mL). To this solution was added hydrochloric acid (20 mL, 6.0 N) over a period of about 5 min. The mixture was stirred at room temperature for about 1 hour and concentrated under reduced pressure. The residue was recrystallized from ethanol at 0° C. to yield 3.20 g (42.7% isomer recovery) of 98% diastereomerically pure dihydrochloric acid salt (based on HPLC peak areas). Microanalysis: Calc.: C 68.64%, H 7.76%, N 5.72%; Found: C 68.79%, H 8.07%, N 5.55%.

EXAMPLE 9

N-[3(S)-[N,N-bis(phenylmethyl)amino]-2(R)-hydroxy-4-phenylbutyl]-N-isobutylamine·toluenesulfonic acid salt Crude 3(S)-[N,N-bis(phenylmethyl) amino]-1-(2-methylpropyl)amino-4-phenylbutan-2(R)-ol (5.0 g, which contains about 3.18 g (7.63 mmol) of 3(S),2(R) isomer and about 0.56 g (1.35 mmol) of 3(S),2(S) isomer} was dissolved in methyl-tert-butylether (10.0 mL). To this solution was added a solution of toluenesulfonic acid (2.28 g, 12 mmol) in methyl-tert-butylether (2.0 mL) and methanol (2.0 mL) over a period of about 5 min. The mixture was stirred at room temperature for about 2 hours and concentrated under reduced pressure. The residue was recrystallized from methyl-tert-butylether and heptane at 0° C., filtered, washed with cold heptane and dried in vacuo to yield 1.85 g (40.0% isomer recovery) of 97% diastereomerically pure monotoluenesulfonic acid salt (based on HPLC peak areas).

EXAMPLE 10

N-[3(S)-[N,N-bis(phenylmethyl)amino]-2(R)-hydroxy-4-phenylbutyl]-N-isobutylamine·methanesulfonic acid salt Crude 3(S)-[N,N-bis(phenylmethyl) amino]-1-(2-methylpropyl)amino-4-phenylbutan-2(R)-ol (10.68 g, which contains about 6.85 g (16.44 mmol) of 3(S),2(R) isomer and about 1.21 g (2.90 mmol) of 3(S),2(S) isomer} was dissolved in tetrahydrofuran (10.0 mL). To this solution was added methanesulfonic acid (1.25 mL, 19.26 mmol). The mixture was stirred at room temperature for about 2 hours and concentrated under reduced pressure. The oily residue was recrystallized from methanol and water at 0° C., filtered, washed with cold methanol/water (1:4) and dried in vacuo to yield 2.40 g (28.5% isomer recovery) of 98% diastereomerically pure monomethanesulfonic acid salt (based on HPLC peak areas).

EXAMPLE 11

3S-[N,N-Bis(phenylmethyl)amino]-1-(3-methylbutyl)amino-4-phenylbutan-2R-ol

Example 4 was followed using isoamylamine instead of isobutylamine to prepare 3S-[N,N-Bis(phenylmethyl)amino]-1-(3-methylbutyl)amino-4-phenylbutan-2R-ol and 3S-[N,N-Bis(phenylmethyl)amino]-1-(3-methylbutyl)amino-4-phenylbutan-2s-ol in comparable yields to that of Example 4. The crude amine was used in the next step without further purification.

EXAMPLE 12

N-[3S-[N,N-Bis(phenylmethyl)aminol]-2R-hydroxy-4-phenyl butyl]-N'-(1,1-dimethylethyl)-N-(2-methylpropyl)urea A solution of the crude 3S-[N,N-bis(phenylmethyl)amino]-1-(2-methylpropyl)amino-4-phenylbutan-2R-ol (446.0 g, 1.1 mol) from Example 4 in tetrahydrofuran (6 L) (or ethyl acetate) was cooled to 8° C. t-Butyl isocyanate (109.5 g, 1.1 mol) was then added to the solution of the amine from an addition funnel at a rate that maintained the temperature between 10–12° C. (addition time was about 10 min). The external cooling was stopped and the reaction was warmed to 18° C. after 30 min. The solution was transferred directly from the reactor to a rotary evaporator flask (10 L) through a teflon tube using vacuum and then concentrated. The flask was heated in a 50° C. water bath during the 2 hours required for the distillation of the solvent. The brown residue was dissolved in ethyl acetate (3 L), washed with 5% aq citric acid solution (1×1.2 L), water (2×500 mL), brine (1×400 mL), dried over magnesium sulfate (200 g) and filtered. The volume of product solution was reduced to 671 mL over 2 h on a rotary evaporator at 50° C. The concentrate was stirred and diluted with 1.6 L of hexane. The mixture was cooled to 12° C. and stirred for 15 hours. The product crystals were isolated by filtration, washed with 10% ethyl acetate/hexane (1×500 mL), hexane (1×200 mL) and dried in vacuo (2 mm) at 50° C. for 1 hour to give 248 g of N-[3S-[N,N-bis-(phenylmethyl)amino]-2R-hydroxy-4-phenylbutyl]-N'-(1,1-dimethylethyl)-N-(2-methylpropyl)-urea. The mother liquor and washes were combined and concentrated on a rotary evaporator to give 270 g of a brown oil. This material was dissolved in ethyl acetate (140 mL) at 50° C. and diluted with hexane (280 mL) and seeded with crystals of the first crop product (20 mg). The mixture was cooled in an ice bath and stirred for 1 h. The solid was isolated by filtration, washed with 10% ethyl acetate/hexane (1×200 mL) and dried in vacuo (2 mm) at 50° C. for 1 h to give 55.7 g of 11 as the second crop (49% overall yield). Mp 126° C.; [α]D25=−59.0° (c=1.0, CH2Cl2), TLC: Rf 0.31 (silica gel, 25% ethyl acetate/hexane).

An analytical sample of the minor diastereomer, N-[3S-[N,N-bis(phenylmethyl)amino]-2S-hydroxy-4-phenylbutyl]-N'-(1,1-dimethylethyl)-N-(2-methylpropyl)urea was isolated by silica-gel chromatography (10–15% ethyl acetate/hexane) in an earlier experiment and characterized.

EXAMPLE 13

N-[3S-[N,N-Bis(phenylmethyl)amino]-2R-hydroxy-4-phenylbutyl]-N'-(1,1-dimethylethyl)-N-(3-methylbutyl)urea The crude product from Example 11 was reacted with t-butylisocyanate following the method of Example 12 to prepare N-[3S-[N,N-Bis(phenylmethyl)amino]-2R-hydroxy-4-phenylbutyl]-N'-(1,1-dimethylethyl)-N-(3-methylbutyl)urea and N-[3S-[N,N-Bis(phenylmethyl)amino]-2S-hydroxy-4-phenylbutyl]-N'-(1,1-dimethylethyl)-N-(3-methylbutyl)urea in comparable yields to that of Example 12.

EXAMPLE 14

N-[3S-Amino-2R-hydroxy-4-phenylbutyl]-N'-(1,1-dimethylethyl)-N-(2-methylpropyl)urea N-[3S-[N,N-Bis(phenylmethyl)amino]-2R-hydroxy-4-phenylbutyl]-N'-(1,1-dimethylethyl)-N-(2-methylpropyl)urea (125.77 g, 0.244 mol) from Example 12 was dissolved in ethanol (1.5 L) (or methanol) and 20% palladium hydroxide on carbon (18.87 g) (or 4% palladium on carbon) was added to the solution under nitrogen. The mixture was stirred at ambient temperature under a hydrogen atmosphere at 60 psi for approximately 8 hours. The catalyst was removed by filtration and the filtrate was concentrated to give 85 g of N-[3S-Amino-2R-hydroxy-4-phenylbutyl]-N'-(1,1-dimethylethyl)-N-(2-methylpropyl)urea as a colorless oil.

EXAMPLE 15

N-[3S-Amino-2R-hydroxy-4-phenylbutyl]-N'-(1,1-dimethylethyl)-N-(3-methylbutyl)urea N-[3S-[N,N-Bis(phenylmethyl)amino]2R-hydroxy-4-phenylbutyl]-N'-(1,1-dimethylethyl)-N-(3-methylbutyl)urea from Example 13 was hydrogenated following the method of Example 14 to prepare N-[3S-Amino-2R-hydroxy-4-phenylbutyl]-N'-(1,1-dimethylethyl)-N-(3-methylbutyl)urea in comparable yields to Example 14.

EXAMPLE 16

N-benzyl-L-phenylalaninol

METHOD 1:

L-Phenylalaninol (89.51 g, 0.592 moles) was dissolved in 375 mL of methanol under inert atmosphere, 35.52 g (0.592 moles) of glacial acetic acid and 50 mL of methanol was added followed by a solution of 62.83 g (0.592 moles) of benzaldehyde in 100 mL of methanol. The mixture was cooled to approximately 15° C. and a solution of 134.6 g (2.14 moles) of sodium cyanoborohydride in 700 mL of methanol was added in approximately 40 minutes, keeping the temperature between 15° C. and 25° C. The mixture was stirred at room temperature for 18 hours. The mixture was concentrated under reduced pressure and partitioned between 1 L of 2M ammonium hydroxide solution and 2 L of ether. The ether layer was washed with 1 L of 1M ammonium hydroxide solution, twice with 500 mL water, 500 mL of brine and dried over magnesium sulfate for 1 hour. The ether layer was filtered, concentrated under reduced pressure and the crude solid product was recrystallized from 110 mL of ethyl acetate and 1.3 L of hexane to give 115 g (81% yield) of N-benzyl-L-phenylalaninol as a white solid.

METHOD 2:

L-Phenylalaninol (5 g, 33 mmoles) and 3.59 g (33.83 mmoles) of benzaldehyde were dissolved in 55 mL of 3A ethanol under inert atmosphere in a Parr shaker and the mixture was warmed to 60° C. for 2.7 hours. The mixture was cooled to approximately 25° C. and 0.99 g of 5% platinum on carbon was added and the mixture was hydrogenated at 60 psi of hydrogen and 40° C. for 10 hours. The catalyst was filtered off, the product was concentrated under reduced pressure and the crude solid product was recrystallized from 150 mL of heptane to give 3.83 g (48% yield) of N-benzyl-L-phenylalaninol as a white solid.

EXAMPLE 17

N-(t-Butoxycarbonyl)-N-benzyl-L-phenylalaninol

N-benzyl-L-phenylalaninol (2.9 g, 12 mmoles) from Example 16 was dissolved in 3 mL of triethylamine and 27 mL of methanol and 5.25 g (24.1 mmoles) of di-tert-butyl dicarbonate was added. The mixture was warmed to 60° C. for 35 minutes and concentrated under reduced pressure. The residue was dissolved in 150 mL of ethyl acetate and washed twice with 10 mL of cold (0–5° C.), dilute hydrochloric acid (pH 2.5 to 3), 15 mL of water, 10 mL of brine, dried over magnesium sulfate, filtered and concentrated under reduced pressure. The crude product oil was purified by silica gel chromatography (ethyl acetate: hexane, 12:3 as eluting solvent) to give 3.98 g (97% yield) of colorless oil.

EXAMPLE 18

N-(t-Butoxycarbonyl)-N-benzyl-L-phenylalaninal

METHOD 1:
To a solution of 0.32 g (0.94 mmoles) of N-(t-Butoxycarbonyl)-N-benzyl-L-phenylalaninol from Example 17 in 2.8 mL of toluene was added 2.4 mg (0.015 mmoles) of 2,2,6,6-tetramethyl-1-1piperidinyloxy, free radical (TEMPO), 0.1 g (0.97 mmoles) of sodium bromide, 2.8 mL of ethyl acetate and 0.34 mL of water. The mixture was cooled to 0° C. and an aqueous solution of 4.2 mL of 5% household bleach containing 0.23 g (3.0 mL, 2.738 mmoles) of sodium bicarbonate was added slowly over 30 minutes. The mixture was stirred at 0° C. for 10 minutes. Three more additions (0.4 mL each) of bleach was added followed by stirring for 10 minutes after each addition to consume all the stating material. The two phase mixture was allowed to separate. The aqueous layer was extracted twice with 8 mL of toluene. The combined organic layer was washed with 1.25 mL of a solution containing 0.075 g of potassium iodide, sodium bisulfate(0.125 g) and water(1.1 mL), 1.25 mL of 10% aqueous sodium thiosulfate solution, 1.25 mL of pH 7 phosphate buffer and 1.5 mL of brine solution. The organic solution was dried over magnesium sulfate, filtered and concentrated under reduced pressure to give 0.32 g (100% yield) of N-(t-Butoxycarbonyl)-N-benzyl-L-phenylalaninal.
METHOD 2:
To a solution of 2.38 g (6.98 mmoles) of N-(t-butoxycarbonyl)-N-benzyl-L-phenylalaninol from Example 17 in 3.8 mL (27.2 mmoles) of triethylamine at 10° C. was added a solution of 4.33 g (27.2 mmoles) of sulfur trioxide pyridine complex in 17 mL of dimethyl sulfoxide. The mixture was warmed to room temperature and stirred for one hour. Water (16 mL) was added and the mixture was extracted with 20 mL of ethyl acetate. The organic layer was washed with 20 mL of 5% citric acid, 20 mL of water, 20 mL of brine, dried over magnesium sulfate and filtered. The filtrate was concentrated under reduced pressure to give 2.37 g (100% yield) of N-(t-Butoxycarbonyl)-N-benzyl-L-phenylalaninal.

EXAMPLE 19

N, αS-Bis(phenylmethyl)-N-(t-butoxycarbonyl)-2S-oxiranemethanamine

METHOD 1:
A solution of 2.5 g (7.37 mmoles) of N-(t-butoxycarbonyl)-N-benzyl-L-phenylalaninal from Example 18 and 0.72 mL of chloroiodomethane in 35 mL of THF was cooled to −78° C. A 4.64 mL of a solution of n-butyllithium (1.6 M in hexane, 7.42 mmoles) was added slowly, keeping the temperature below −70° C. The mixture was stirred for 10 minutes between −70 to −75° C. Two additional portions of 0.22 mL of chloroiodomethane and 1.4 mL of n-butyllithium was added sequentially and the mixture was stirred for 10 minutes between −70 to −75° C. after each addition. Four additional portions of 0.11 mL of chloroiodomethane and 0.7 mL of n-butyllithium was added sequentially and the mixture was stirred for 10 minutes between −70 to −75° C. after each addition. The mixture was warmed to room temperature for 3.5 hours. The product was quenched at below 5° C. with 24 mL of ice-cold water. The biphasic layers were separated and the aqueous layer was extracted twice with 30 mL of ethyl acetate. The combined organic layers was washed three times with 10 mL water, then with 10 mL brine, dried over sodium sulfate, filtered and concentrated under reduced pressure to give 2.8 g of a yellow crude oil. This crude oil (>100% yield) is a mixture of the diastereomeric epoxides N,αS-bis(phenylmethyl)-N-(t-butoxycarbonyl)-2S-oxiranemethanamine and N, αS-bis(phenylmethyl)-N-(t-butoxycarbonyl)-2R-oxiranemethanamine. The crude mixture is used directly in the next step without purification.
METHOD 2:
To a suspension of 2.92 g (13.28 mmoles) of trimethylsulfoxonium iodide in 45 mL of acetonitrile was added 1.49 g (13.28 mmoles) of potassium t-butoxide. A solution of 3.0 g (8.85 mmoles) of N-(t-butoxycarbonyl)-N-benzyl-L-phenylalaninal from Example 18 in 18 mL of acetonitrile was added and the mixture was stirred at room temperature for one hour. The mixture was diluted with 150 mL of water and extracted twice with 200 mL of ethyl acetate. The organic layers were combined and washed with 100 mL water, 50 mL brine, dried over sodium sulfate, filtered and concentrated under reduced pressure to give 3.0 g of a yellow crude oil. The crude product was purified by silica gel chromatography (ethyl acetate/hexane: 1:8 as eluting solvent) to give 1.02 g (32.7% yield) of a mixture of the two diastereomers N, αS-bis(phenylmethyl)-N-(t-butoxycarbonyl)-2S-oxiranemethanamine and N, αS-bis(phenylmethyl)-N-(t-butoxycarbonyl)-2R-oxiranemethanamine.
METHOD 3:
To a suspension of 0.90 g (4.42 mmoles) of trimethylsulfonium iodide in 18 mL of acetonitrile was added 0.495 g (4.42 mmoles) of potassium t-butoxide. A solution of 1.0 g (2.95 mmoles) of N-(t-butoxycarbonyl)-N-benzyl-L-phenylalaninal from Example 18 in 7 mL of acetonitrile was added and the mixture was stirred at room temperature for one hour. The mixture was diluted with 80 mL of water and extracted twice with 80 mL of ethyl acetate. The organic layers were combined and washed with 100 mL water, 30 mL brine, dried over sodium sulfate, filtered and concentrated under reduced pressure to give 1.04 g of a yellow crude oil. The crude product was a mixture of the two diastereomers N, αS-bis(phenylmethyl)-N-(t-butoxycarbonyl)-2S-oxiranemethanamine and N, αS-bis(phenylmethyl)-N-(t-butoxycarbonyl)-2R-oxiranemethanamine.

EXAMPLE 20

3S- [N-(t-Butoxycarbonyl)-N-(phenylmethyl) amino]- 1-(2-methylpropyl)amino-4-phenylbutan-2R-ol To a solution of 500 mg (1.42 mmoles) of the crude epoxide from Example 19 in 0.98 mL of isopropanol was added 0.71 mL (7.14 mmoles) of isobutylamine. The mixture was warmed to reflux at 85° C. to 90° C. for 1.5 hours. The mixture was concentrated under reduced pressure and the product oil was purified by silica gel chromatography (chloroform:methanol, 100:6 as eluting solvents) to give 330 mg of 3S-[N-(t-butoxycarbonyl)-N-(phenylmethyl)amino]-1-(2-methylpropyl)amino-4-phenylbutan-2R-ol as a colorless oil (54.5% yield). 3S-[N-(t-Butoxycarbonyl)-N-(phenylmethyl)amino]-1-(2-methylpropyl)amino-4-phenylbutan-2S-ol was also isolated. When purified N,αS-bis(phenylmethyl)-N-(t-butoxycarbonyl)-2S-oxiranemethanamine was used as starting material, 3S-[N-(t-butoxycarbonyl)-N-(phenylmethyl)amino]-1-(2-methylpropyl)amino-4-phenylbutan-2R-ol was isolated after purification by chromatography in an 86% yield.

EXAMPLE 21

N-[3S-[N-(t-Butoxycarbonyl)-N-(phenylmethyl) amino]-2R-hydroxy-4- phenylbutyl]-N'-(1,1-dimethylethyl)-N-(2-methylpropyl)urea To a solution of 309 mg (0.7265 mmoles) of 3S-[N-(t-butoxycarbonyl)-N-(phenylmethyl)amino]-1-(2-methylpropyl)amino-4-phenylbutan-2R-ol from Example 20 in 5 mL of THF was added 0.174 mL (1.5 mmoles) of t-butylisocyanate. The mixture was stirred at room temperature for 1.5 hours. The product was concentrated under reduced pressure to give 350 mg (92% yield) of a white solid crude product. The crude product was purified by silica gel chromatography (ethyl acetate/hexane: 1:4 as eluting solvents) to give 324 mg of N-[3S-[N-(t-butoxycarbonyl)-N-(phenylmethyl)amino]-2R-hydroxy-4-phenylbutyl]-N'-(1,1-dimethylethyl)-N-(2-methylpropyl)urea as a white solid (85.3% yield).

EXAMPLE 22

3S-[N-(t-Butoxycarbonyl)-N-(phenylmethyl)amino]-2S-hydroxy-4-phenylbutyronitrile A solution of 7.0 g (20.65 mmoles) of N-(t-butoxycarbonyl)-N-benzyl-L-phenylalaninal from Example 18 in 125 mL of THF was cooled to −5° C. A solution of 12.96 g of sodium bisulfite in 68 mL of water was added over 40 minutes, keeping the temperature below 5° C. The mixture was stirred for 3 hours at 0 to 5° C. An additional 1.4 g of sodium bisulfite was added and the mixture was stirred for another two hours. Sodium cyanide (3.3 g, 82.56 mmoles) was added to the bisulfite product at 0 to 5° C. and the mixture was stirred at room temperature for 16 hours. The biphasic mixture was extracted with 150 mL of ethyl acetate. The aqueous layer was extracted twice each with 100 mL of ethyl acetate. The combined organic layers was washed twice with 30 mL water, twice with 25 mL brine, dried over sodium sulfate, filtered and concentrated under reduced pressure to give 7.5 g (100% crude yield of both diastereomers) of crude oil. The crude oil was purified by silica gel chromatography (ethyl acetate: hexane, 1:4 as eluting solvents) to give 5.725 g (76% yield) of 3S-[N-(t-butoxycarbonyl)-N-(phenylmethyl)amino]-2S-hydroxy-4-phenylbutyronitrile as the major later eluting diastereomer and 0.73 g (9.6% yield) of 3S-[N-(t-butoxycarbonyl)-N-(phenylmethyl)amino]-2R-hydroxy-4-phenylbutyronitrile as the minor diastereomer. The combined yields of both isomers of cyanohydrins is 85.6% yield.

EXAMPLE 23

3S-[N-(t-Butoxycarbonyl)-N-(phenylmethyl)amino]-1-amino-4-phenylbutan-2R-ol

To a solution of 205.5 mg (0.56 mmoles) of 3S-[N-(t-butoxycarbonyl)-N-(phenylmethyl)amino]-2S-hydroxy-4-phenylbutyronitrile from Example 22 in 4 mL of THF was added 2.4 mL of a solution of borane in THF (1.0 M, 4 mmoles). The mixture was stirred at room temperature for 30 minutes. An additional 1.4 mL of borane in THF was added and the mixture was stirred for another 30 minutes. The mixture was cooled to 0° C. and 2.0 mL of cold(0–5° C.) water was added slowly. The mixture was warmed to room temperature and stirred for 30 minutes. The product was extracted twice with 30 mL of ethyl acetate. The organic layers were combined and washed with 4 mL water, 4 mL brine, dried over sodium sulfate, filtered and concentrated under reduced pressure to give 200 mg of 3S-[N-(t-butoxycarbonyl)-N-(phenylmethyl)amino]-1-amino-4-phenylbutan-2R-ol as a white solid (96.4% yield).

EXAMPLE 24

3S-[N-(t-Butoxycarbonyl)-N-(phenylmethyl)amino]-1-(2-methylpropyl)amino-4-phenylbutan-2R-ol To a solution of 2.41 g (6.522 mmoles) of 3S-[N-(t-butoxycarbonyl)-N-(phenylmethyl)amino]-1-amino-4-phenylbutan-2R-ol from Example 23 in 40 mL of methanol was added 0.592 mL (6.522 mmoles) of isobutyraldehyde and 0.373 mL (6.522 mmoles) of acetic acid. The mixture was stirred for 10 minutes. Sodium cyanoborohydride (1.639 g, 26 mmoles) was added and the mixture was stirred for 16 hours at room temperature. The product mixture was concentrated under reduced pressure and partitioned between 150 mL of ethyl acetate and 50 mL of 1.5M ammonium hydroxide. The organic layer was washed twice with 20 mL water, twice with 20 mL brine, dried over sodium sulfate, filtered and concentrated to an yellow oil. The crude product was purified by silica gel chromatography (chloroform: methanol, 100:6 as eluting solvents) to give 2.326 g of 3S-[N-(t-butoxycarbonyl)-N-(phenylmethyl)amino]-1- (2-methylpropyl)amino-4-phenylbutan-2R-ol as a colorless oil (88.8% yield).

EXAMPLE 25

N-[3S-[N-(t-Butoxycarbonyl)-N-(phenylmethyl) amino]-2R-hydroxy-4-phenylbutyl]-N'-(1,1-dimethylethyl)-N-(2-methylpropyl)urea To a solution of 309 mg (0.7265 mmoles) of 3S-[N-(t-butoxycarbonyl)-N-(phenylmethyl)amino]-1-(2-methylpropyl)amino-4-phenylbutan-2R-ol from Example 24 in 5 mL of THF was added 0.174 mL(1.5 mmoles) of t-butylisocyanate. The mixture was stirred at room temperature for 1.5 hours. The product was concentrated under reduced pressure to give 350 mg (92% yield) of a white solid crude product. The crude product was purified by silica gel chromatography (ethyl acetate/hexane: 1:4 as eluting solvents) to give 324 mg of N-[3S-[N-(t-butoxycarbonyl)-N-(phenylmethyl)amino]-2R-hydroxy-4-phenylbutyl]-N'-

(1, 1-dimethylethyl)-N-(2-methylpropyl)urea as a white solid (85.3% yield).

EXAMPLE 26

N-[3S-[N-(Phenylmethyl)amino]-2R-hydroxy-4-phenylbutyl]-N'-(1,1-dimethylethyl)-N-(2-methylpropyl)urea To a solution of 210 mg (0.4 mmoles) of N-[3S-[N-(t-Butoxycarbonyl)-N-(phenylmethyl)amino]-2R-hydroxy-4-phenylbutyl]-N'-(1,1-dimethylethyl)-N-(2-methylpropyl)urea from Example 25 in 5.0 mL of THF was added 5 mL of 4N hydrochloric acid. The mixture was stirred at room temperature for two hours. The solvents were removed under reduced pressure to give 200 mg (100%) of N-[3S-[N-(phenylmethyl)amino]-2R-hydroxy-4-phenylbutyl]-N'-(1,1-dimethylethyl)-N-(2-methylpropyl)urea as a white solid.

EXAMPLE 27

N-[3S-Amino-2R-hydroxy-4-phenylbutyl]-N'-(1,1-dimethylethyl)-N-(2-methylpropyl)urea To a solution of 200 mg (0.433 mmoles) of N-[3S-[N-(phenylmethyl)amino]-2R-hydroxy-4-phenylbutyl]-N'-(1,1-dimethylethyl)-N-(2-methylpropyl)urea from Example 26 in 7 mL of 3A ethanol was added 0.05 g of 20% palladium on carbon. The mixture was hydrogenated at 40° C. for 1.8 hours at 5 psi followed by hydrogenation at 60 psi at room temperature for 22 hours. The catalyst was filtered and the solvent and by-product were removed under reduced pressure to give 150 mg (93.4% yield) of N-[3S-amino-2R-hydroxy-4-phenylbutyl]-N'-(1, 1-dimethylethyl)-N-(2-methylpropyl)urea as a white solid.

EXAMPLE 28

3S-(N-t-Butoxycarbonyl) amino-4-phenylbutan-1, 2R-diol

To a solution of 1 g (3.39 mmoles) of 2S-(N-t-butoxycarbonyl)amino-1S-hydroxy-3-phenylbutanoic acid (commercially available from Nippon Kayaku, Japan) in 50 mL of THF at 0° C. was added 50 mL of borane-THF complex (liquid, 1.0 M in THF), keeping the temperatures below 5° C. The reaction mixture was warmed to room temperature and stirred for 16 hours. The mixture was cooled to 0° C. and 20 mL of water was added slowly to destroy the excess $BH_3$ and to quench the product mixture, keeping the temperature below 12° C. The quenched mixture was stirred for 20 minutes and concentrated under reduced pressure. The product mixture was extracted three times with 60 mL of ethyl acetate. The organic layers were combined and washed with 20 mL of water, 25 mL of saturated sodium chloride solution and concentrated under reduced pressure to give 1.1 g of crude oil. The crude product was purified by silica gel chromatography (chloroform/methanol, 10:6 as eluting solvents) to give 900 mg (94.4% yield) of 3S-(N-t-butoxycarbonyl)amino-4-phenylbutan-1,2R-diol as a white solid.

EXAMPLE 29

3S-(N-t-Butoxycarbonyl)amino-2R-hydroxy-4-phenylbut-1-yl Toluenesulfonate

To a solution of 744.8 mg (2.65 mmoles) of 3S-(N-t-butoxycarbonyl)amino-4-phenylbutan-1,2R-diol from Example 28 in 13 mL of pyridine at 0° C. was added 914 mg of toluenesulfonyl chloride in one portion. The mixture was stirred at 0° C. to 5° C. for 5 hours. A mixture of 6.5 mL of ethyl acetate and 15 mL of 5% aqueous sodium bicarbonate solution was added to the reaction mixture and stirred for 5 minutes. The product mixture was extracted three times with 50 mL of ethyl acetate. The organic layers were combined and washed with 15 mL of water, 10 mL of saturated sodium chloride solution and concentrated under reduced pressure to give about 1.1 g of a yellow chunky solid. The crude product was purified by silica gel chromatography (ethyl acetate/hexane 1:3 as eluting solvents) to give 850 mg (74% yield) of 3S-(N-t-butoxycarbonyl)amino-2R-hydroxy-4-phenylbut-1-yl toluenesulfonate as a white solid.

EXAMPLE 30

3S-[N-(t-Butoxycarbonyl)amino]-1-(2-methylpropyl)amino-4-phenylbutan-2R-ol

To a solution of 90 mg (0.207 mmoles) of 3S-(N-t-butoxycarbonyl)amino-2R-hydroxy-4-phenylbut-1-yl toluenesulfonate from Example 29 in 0.143 mL of isopropanol and 0.5 mL of toluene was added 0.103 mL (1.034 mmoles) of isobutylamine. The mixture was warmed to 80 to 85° C. and stirred for 1.5 hours. The product mixture was concentrated under reduced pressure at 40 to 50° C. and purified by silica gel chromatography (chloroform/methanol, 10:1 as eluting solvents) to give 54.9 mg (76.8% yield) of 3S-[N-(t-butoxycarbonyl)amino]-1-(2-methylpropyl)amino-4-phenylbutan-2R-ol as a white solid.

EXAMPLE 31

N-[3S-[N-(t-Butoxycarbonyl)amino]-2R-hydroxy-4-phenylbutyl]-N'-(1,1-dimethylethyl)-N-(2-methylpropyl)urea To a solution of 0.1732 g (0.516 mmoles) of 3S-[N-(t-butoxycarbonyl)amino]-1-(2-methylpropyl)amino-4-phenylbutan-2R-ol from Example 30 in 5 mL of ethyl acetate at 0° C. was added 1.62 mL (12.77 mmoles) of t-butylisocyanate and the mixture was stirred for one hour. The product was concentrated under reduced pressure and purified by silica gel chromatography (chloroform/methanol, 100:1.5 as eluting solvents) to give 96 mg (42.9% yield) of N-[3S-[N-(t-butoxycarbonyl)amino]-2R-hydroxy-4-phenylbutyl]-N'-(1,1-dimethylethyl)-N-(2-methylpropyl)urea as a white solid.

EXAMPLE 32

N-[3S-amino-2R-hydroxy-4-phenylbutyl]-N'-(1,1-dimethylethyl)-N-(2-methylpropyl)urea To a solution of 10 mg (0.023 mmoles) of N-[3S-[N-(t-butoxycarbonyl)amino]-2R-hydroxy-4-phenylbutyl]-N'-(1, 1-dimethylethyl)-N-(2-methylpropyl)urea from Example 31 in 1 mL of methanol at 0° C. was added 1.05 mL of a 4M hydrogen chloride in methanol and the mixture was stirred at room temperature for 45 minutes. The product was concentrated under reduced pressure. The residue was dissolved 5 mL of methanol and concentrated under reduced pressure. This operation was repeated three times to remove water form the product, after which 8.09 mg (95.2% yield) of N-[3S-amino-2R-hydroxy-4-phenylbutyl]-N'-(1,1-dimethylethyl)-N-(2-methylpropyl)urea hydrochloride salt was obtained as a white solid.

EXAMPLE 33

3S-(N,N-Dibenzyl)amino-2S-hydroxy-4-phenylbutyronitrile, O-trimethylsilyl ether

To a solution of 24.33 g (73.86 mmol) of 2S-(N,N-dibenzyl)amino-3-phenylpropanal in 740 mL of anhydrous methylene chloride at −20 C under a nitrogen atmosphere, was added 11.8 mL (8.8 g, 88.6 mmol) of trimethylsilylcyanide, then 19.96 g (88.6 mmol) of anhydrous zinc bromide. After 4 hours at −15 C, and 18 hours at room temperature, the solvent was removed under reduced pressure, ethyl acetate was added, washed with water, brine, dried over magnesium sulfate, filtered and concentrated to afford 31.3 g of a brown oil, which was identified as a 95:5 mixture of 3S-(N,N-dibenzyl)amino-2S-hydroxy-4-phenylbutyronitrile, O-trimethylsilyl ether, m/e=429(M+H) and 3S-(N,N-dibenzyl)amino-2R-hydroxy-4-phenylbutyronitrile, O-trimethylsilyl ether, respectively.

EXAMPLE 34

3S-(N,N-Dibenzyl)amino-2S-hydroxy-4-phenylbutyronitrile

A solution of 10.4 g (24.3 mmol) of the crude 95:5 mixture of 3S-(N,N-dibenzyl)amino-2S-hydroxy-4-phenylbutyronitrile, O-trimethylsilyl ether, and 3S-(N,N-dibenzyl)amino-2R-hydroxy-4-phenylbutyronitrile, O-trimethylsilyl ether from Example 33 in 40 mL of methanol, was added to 220 mL of 1N hydrochloric acid with vigorous stirring. The resulting solid was collected, dissolved in ethyl acetate, washed with aqueous sodium bicarbonate, brine, dried over anhydrous magnesium sulfate, filtered and concentrated to afford 8.04 g of crude product. This was recrystallized from ethyl acetate and hexane to afford pure 3S-(N,N-dibenzyl)amino-2S-hydroxy-4-phenylbutyronitrile, m/e=357 (M+H).

EXAMPLE 35

3S-(N,N-Dibenzyl)amino-2R-hydroxy-4-phenylbutylamine

METHOD 1:

A solution of 20.3 g (47.3 mmol) of the crude 95:5 mixture of 3S-(N,N-dibenzyl)amino-2S-hydroxy-4-phenylbutyronitrile, O-trimethylsilyl ether, and 3S-(N,N-dibenzyl)amino-2R-hydroxy-4-phenylbutyronitrile, O-trimethylsilyl ether from Example 34 in 20 mL of anhydrous diethyl ether, was added to 71 mL (71 mmol) of a 1M solution of lithium aluminum hydride in diethyl ether at reflux. After the addition, the reaction was refluxed for 1 hour, cooled to 0 C, and quenched by the careful addition of 2.7 mL of water, 2.7 mL of 15% aqueous sodium hydroxide, and 8.1 mL of water. The resulting solids were removed by filtration and the filtrate washed with water, brine, dried over magnesium sulfate, filtered and concentrated to afford 13.8 g of crude material, which was recrystallized from tetrahydrofuran and isooctane to afford 10.6 g of 3S-(N,N-dibenzyl)amino-2R-hydroxy-4-phenylbutylamine, Mp=46–49 C, m/e=361 (M+H), which was contaminated by approximately 2% of 3S-(N,N-dibenzyl)amino-2S-hydroxy-4-phenylbutylamine.

METHOD 2:

To 15.6 mL (60.4 mmol) of 70% sodium bis (methoxyethoxy)aluminum hydride in toluene, was added 15 mL of anhydrous toluene, and then after cooling to 0 C, a solution of 20.0 g (46 mmol) of the crude 95:5 mixture of 3S-(N,N-dibenzyl)amino-2S-hydroxy-4-phenylbutyronitrile, O-trimethylsilyl ether, and 3S-(N,N-dibenzyl)amino-2R-hydroxy-4-phenylbutyronitrile, O-trimethylsilyl ether from Example 34 in 10 mL of anhydrous toluene, at a rate so as to maintain the temperature below 15° C. After 2.5 hours at room temperature, the reaction was quenched by the careful addition of 200 mL of 5% aqueous sodium hydroxide. The solution was diluted with ethyl acetate, washed with 5% sodium hydroxide, sodium tartrate solution, brine, dried over magnesium sulfate, filtered and concentrated to afford 16.6 g of crude product, which was assayed by HPLC and shown to contain 87% of 3S-(N,N-dibenzyl)amino-2R-hydroxy-4-phenylbutylamine.

EXAMPLE 36

N-[3S-(N,N-Dibenzyl)amino-2R-hydroxy-4-phenylbutyl]-N'-(1,1-dimethylethyl)-N-(3-methylbutyl)urea Step 1:

To a solution of 1.0 g (2.77 mmol) of 3S-(N,N-dibenzyl) amino-2R-hydroxy-4-phenylbutylamine from Example 35 in 4.6 mL of ethanol, was added 0.3 mL (0.24g, 2.77 mmol) of isovaleraldehyde. After 1 hour at room temperature, the ethanol was removed under reduced pressure, 4 mL of ethyl acetate was added and the solution purged with nitrogen. To the solution was added 360 mg of 5% platinum on carbon catalyst, the solution purged with 40 psig of hydrogen and then maintained under 40 psig of hydrogen for 20 hours. The solution was purged with nitrogen, the catalyst removed by filtration and the solvent removed under reduced pressure to afford 473 mg of the crude product.

Step 2:

The crude product from Step A was directly dissolved in 5.4 mL of ethyl acetate and 109 mg (1.1 mmol) of tertiary-butyl isocyanate was added. After 1 hour at room temperature, the solution was washed with 5% citric acid, brine, dried over magnesium sulfate, filtered and concentrated to afford 470 mg of crude product. The crude product was recrystallized from ethyl acetate and isooctane to afford 160 mg of N-[3S-(N,N-Dibenzyl)amino-2R-hydroxy-4-phenylbutyl]-N'-(1,1-dimethylethyl)-N-(3-methylbutyl) urea, Mp=120.4–121.7° C., m/e=530 (M+H).

From the foregoing detailed description, one skilled in the art can easily ascertain the essential characteristics of this invention, and without departing from the spirit and scope thereof, can make various changes and modifications of the invention to adapt it to various uses and conditions.

What is claimed is:

1. Compound represented by the formula:

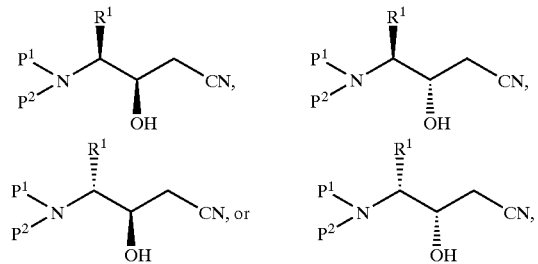

or an organic or inorganic acid salt thereof, wherein:

$R^1$ represents aralkyl radicals, which are optionally substituted with alkyl, halogen, $NO_2$, $OR^9$ or $SR^9$ radicals, where $R^9$ represents hydrogen, alkyl, aryl or aralkyl radicals; and $P^1$ and $P^2$ together with the nitrogen atom to which they are bonded form a 2-isoindolinyl, succinimidyl, maleimidyl, morpholinyl, thiomorpholinyl, piperidinyl, or pyrrolidinyl radical.

2. An organic acid salt of a compound represented by the formula:

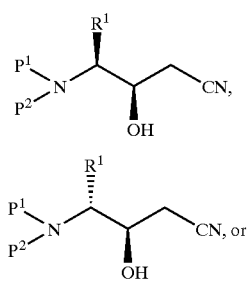

wherein $R^1$ represents alkyl, aryl, cycloalkyl, cycloalkylalkyl or aralkyl radicals, which are optionally substituted with alkyl, halogen, $NO_2$, $OR^9$ or $SR^9$ radicals, where $R^9$ represents hydrogen, alkyl, aryl or aralkyl radicals; and $P^1$ and $P^2$ are each independently acyl, aralkyl, silyl, aralkoxycarbonyl, alkoxycarbonyl, alkylcarbonyl, aralkylcarbonyl, arylcarbonyl or cycloalkenylalkyl radicals; or $P^1$ and $P^2$ together with the nitrogen atom to which they are bonded form a heterocyclic ring system, and wherein the organic acid salt is a salt of acetic acid, camphorsulfonic acid, toluenesulfonic acid, methanesulfonic acid, malic acid, tartaric acid, mandelic acid, trifluoroacetic acid or oxalic acid.

3. An organic acid salt of claim 2, wherein the organic acid is acetic acid, oxalic acid or tartaric acid.

4. An inorganic acid salt of a compound represented by the formula:

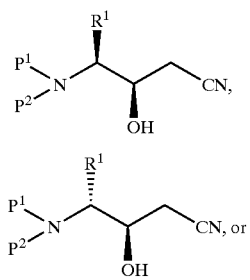

wherein:

$R^1$ represents alkyl, aryl, cycloalkyl, cycloalkylalkyl or aralkyl radicals, which are optionally substituted with alkyl, halogen, $NO_2$, $OR^9$ or $SR^9$ radicals, where $R^9$ represents hydrogen, alkyl, aryl or aralkyl radicals; and $P^1$ and $P^2$ are each independently acyl, aralkyl, silyl, aralkoxycarbonyl, alkoxycarbonyl, aralkylcarbonyl, arylcarbonyl or cycloalkenylalkyl radicals; or $P^1$ and $P^2$ together with the nitrogen atom to which they are bonded form a heterocyclic ring system, and wherein the inorganic acid salt is a salt of hydrochloric acid, hydrobromic acid, phosphoric acid, sulfurous acid or sulfuric acid.

5. An inorganic acid salt of claim 4 wherein the inorganic acid is hydrochloric acid.

6. Compound represented by the formula:

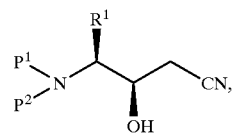

or an organic or inorganic acid salt thereof, wherein:

$R^1$ represents aralkyl radicals which are optionally substituted with alkyl, halogen, $NO_2$, $OR^9$ or $SR^9$ radicals, where $R^9$ represents hydrogen, alkyl, aryl or aralkyl radicals; and $P^1$ and $P^2$ together with the nitrogen atom to which they are bonded form a 2-isoindolinyl, succinimidyl, maleimidyl, morpholinyl, thiomorpholinyl, piperidinyl, or pyrrolidinyl radical.

7. An organic acid salt of a compound represented by the formula:

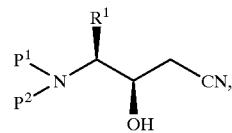

wherein:

$R^1$ represents alkyl, aryl, cycloalkyl, cycloalkylalkyl or aralkyl radicals, which are optionally substituted with alkyl, halogen, $NO_2$, $OR^9$ or $SR^9$ radicals, where $R^9$ represents hydrogen, alkyl, aryl or aralkyl radicals; and $P^1$ and $P^2$ are each independently acyl, aralkyl, silyl, aralkoxycarbonyl, alkoxycarbonyl, alkylcarbonyl, aralkylcarbonyl, arylcarbonyl or cycloalkenylalkyl radicals; or $P^1$ and $P^2$ together with the nitrogen atom to which they are bonded form a heterocyclic ring system, and wherein the organic acid salt is a salt of acetic acid, camphorsulfonic acid, toluenesulfonic acid, methanesulfonic acid, malic acid, tartaric acid, mandelic acid, trifluoroacetic acid of oxalic acid.

8. An organic acid salt of claim 7 wherein the organic acid is acetic acid, oxalic acid or tartaric acid.

9. An inorganic acid salt of a compound represented by the formula:

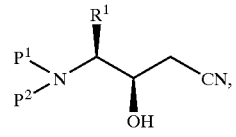

wherein:

$R^1$ represents alkyl, aryl, cycloalkyl, cycloalkylalkyl or aralkyl radicals, which are optionally substituted with alkyl, halogen, $NO_2$, $OR^9$ or $SR^9$ radicals, where $R^9$ represents hydrogen, alkyl, aryl or aralkyl radicals; and $P^1$ and $P^2$ are each independently acyl, aralkyl, silyl, aralkoxycarbonyl, alkoxycarbonyl, alkylcarbonyl, aralkylcarbonyl, arylcarbonyl or cycloalkenylalkyl radicals; or $P^1$ and $P^2$ together with the nitrogen atom to which they are bonded form a heterocyclic ring system, and wherein the inorganic acid salt is a salt of hydrochloric acid, hydrobromic acid, phosphoric acid, sulfurous acid or sulfuric acid.

10. An inorganic acid salt of claim 9 wherein the inorganic acid is hydrochloric acid.

* * * * *